(12) United States Patent
Massing

(10) Patent No.: US 10,662,060 B2
(45) Date of Patent: May 26, 2020

(54) MANUFACTURE OF LIPID-BASED NANOPARTICLES USING A DUAL ASYMMETRIC CENTRIFUGE

(75) Inventor: Ulrich Massing, Merzhausen (DE)

(73) Assignee: Ulrich Massing, Merzhausen (DE)

( * ) Notice: Subject to any disclaimer, the term of this patent is extended or adjusted under 35 U.S.C. 154(b) by 569 days.

(21) Appl. No.: 11/793,732

(22) PCT Filed: Dec. 23, 2005

(86) PCT No.: PCT/EP2005/057157
§ 371 (c)(1),
(2), (4) Date: Nov. 30, 2007

(87) PCT Pub. No.: WO2006/069985
PCT Pub. Date: Jul. 6, 2006

(65) Prior Publication Data
US 2008/0193511 A1  Aug. 14, 2008

(30) Foreign Application Priority Data

Dec. 23, 2004 (EP) ..................................... 04106939

(51) Int. Cl.
| | |
|---|---|
| *B82Y 5/00* | (2011.01) |
| *A61K 9/51* | (2006.01) |
| *A61K 9/127* | (2006.01) |
| *A61K 8/14* | (2006.01) |
| *B01F 9/00* | (2006.01) |

(Continued)

(52) U.S. Cl.
CPC .................. *B82Y 5/00* (2013.01); *A61K 8/14* (2013.01); *A61K 9/1277* (2013.01); *A61K 9/5123* (2013.01); *A61K 9/5192* (2013.01); *A61K 47/6913* (2017.08); *A61Q 19/00* (2013.01); *B01F 9/0001* (2013.01);
(Continued)

(58) Field of Classification Search
CPC .......... A61K 47/48823; A61K 47/6913; A61K 8/14; A61K 9/0073; A61K 9/127; A61K 9/1271; A61K 9/1272; A61K 9/1277; A61K 9/5123; A61K 9/5192
USPC ................................ 366/217, 219, 220, 232
See application file for complete search history.

(56) References Cited

U.S. PATENT DOCUMENTS

| | | | | |
|---|---|---|---|---|
| 300,545 A | * | 6/1884 | Wiegand ........................ | 210/203 |
| 895,173 A | * | 8/1908 | Ecaubert ....................... | 366/235 |

(Continued)

FOREIGN PATENT DOCUMENTS

| | | |
|---|---|---|
| DE | 1151718 | 7/1963 |
| DE | 3825374 A1 | 2/1990 |

(Continued)

OTHER PUBLICATIONS

Massing et al. Dual asymmetric centrifugation (DAC)—A new technique for liposome preparation. Journal of Controlled Release 125 (2008) 16-24.*

(Continued)

*Primary Examiner* — Tony G Soohoo
(74) *Attorney, Agent, or Firm* — Ballard Spahr LLP

(57) ABSTRACT

The invention relates to a method for producing lipid-based nanoparticles using a dual asymmetrical centrifuge, products produced by means of said method, kits for producing said nanoparticles using a dual asymmetrical centrifuge, and accessories for carrying out the inventive method.

34 Claims, 10 Drawing Sheets

(51) Int. Cl.
*A61Q 19/00* (2006.01)
*A61K 47/69* (2017.01)
*A61K 9/00* (2006.01)

(52) U.S. Cl.
CPC ............ *A61K 9/0073* (2013.01); *A61K 9/127* (2013.01); *A61K 9/1271* (2013.01); *A61K 9/1272* (2013.01)

(56) References Cited

U.S. PATENT DOCUMENTS

| | | | | |
|---|---|---|---|---|
| 1,011,929 | A * | 12/1911 | Ecaubert | 494/47 |
| 1,343,091 | A * | 6/1920 | Shearer | 366/217 |
| 2,313,045 | A * | 3/1943 | Brown | 366/217 |
| 3,679,184 | A * | 7/1972 | Woodham et al. | 366/219 |
| 3,778,033 | A * | 12/1973 | Pullman | 366/219 |
| 4,497,581 | A * | 2/1985 | Miller | 366/208 |
| 4,728,197 | A * | 3/1988 | Reinhard | 366/219 |
| 4,776,832 | A * | 10/1988 | Martin et al. | 494/19 |
| 4,814,282 | A * | 3/1989 | Holen et al. | 436/165 |
| 4,861,477 | A | 8/1989 | Kimura | 210/359 |
| 5,151,264 | A | 9/1992 | Samain et al. | 424/1.1 |
| 5,167,448 | A * | 12/1992 | Herold et al. | 366/213 |
| 5,352,037 | A | 10/1994 | Jouvin | 366/219 |
| 5,551,779 | A * | 9/1996 | Gantner et al. | 366/217 |
| 5,620,703 | A | 4/1997 | Reszka | |
| 5,705,196 | A | 1/1998 | Valdivia et al. | 424/497 |
| 5,746,510 | A * | 5/1998 | Mark et al. | 366/217 |
| 6,099,160 | A * | 8/2000 | Flackett | 366/217 |
| 6,126,097 | A | 10/2000 | Chen | |
| 6,361,486 | B1 * | 3/2002 | Gordon | 494/19 |
| 6,709,151 | B2 | 3/2004 | Schmidt | 366/219 |
| 6,733,170 | B2 * | 5/2004 | Mukasa et al. | 366/139 |
| 6,755,565 | B2 * | 6/2004 | Flackett | 366/217 |
| 6,767,126 | B2 * | 7/2004 | Miller | 366/217 |
| 6,770,299 | B1 | 8/2004 | Müller et al. | 424/489 |
| 7,097,348 | B2 * | 8/2006 | Miller | 366/217 |
| 7,261,860 | B1 * | 8/2007 | Vellinger et al. | 422/72 |
| 7,396,152 | B2 * | 7/2008 | Veronneau | 366/217 |
| 7,438,460 | B2 * | 10/2008 | Schmidt et al. | 366/139 |
| 2002/0172091 | A1 | 11/2002 | Hatakeyama | 366/144 |
| 2003/0067838 | A1 * | 4/2003 | Schmidt | 366/219 |
| 2003/0103409 | A1 * | 6/2003 | Mukasa et al. | 366/139 |
| 2003/0198126 | A1 * | 10/2003 | Flackett | 366/217 |
| 2003/0214878 | A1 | 11/2003 | Huckby | 366/217 |
| 2003/0229037 | A1 * | 12/2003 | Massing et al. | 514/44 |
| 2004/0082521 | A1 | 4/2004 | Singh | |
| 2004/0152828 | A1 * | 8/2004 | Brandt et al. | 524/588 |
| 2005/0031679 | A1 * | 2/2005 | Unger et al. | 424/450 |
| 2005/0064026 | A1 * | 3/2005 | Garidel | A61K 9/1272 424/450 |
| 2006/0002228 | A1 * | 1/2006 | Schulz et al. | 366/209 |
| 2006/0039978 | A1 | 2/2006 | Diederichs | 424/484 |
| 2007/0002680 | A1 * | 1/2007 | Vanderbilt et al. | 366/217 |
| 2007/0002681 | A1 * | 1/2007 | Vanderbilt et al. | 366/217 |
| 2007/0002682 | A1 * | 1/2007 | Vanderbilt et al. | 366/217 |
| 2007/0025180 | A1 * | 2/2007 | Ishii | 366/139 |
| 2007/0066748 | A1 * | 3/2007 | Lewandowski et al. | 524/556 |
| 2007/0280038 | A1 * | 12/2007 | Schmidt et al. | 366/139 |
| 2008/0110371 | A1 * | 5/2008 | Hollman et al. | 106/418 |
| 2008/0110372 | A1 * | 5/2008 | Hollman et al. | 106/418 |
| 2008/0115694 | A1 * | 5/2008 | Hollman et al. | 106/418 |
| 2008/0118452 | A1 * | 5/2008 | Hollman et al. | 424/61 |
| 2008/0124575 | A1 * | 5/2008 | Hollman et al. | 428/402 |
| 2009/0264491 | A1 * | 10/2009 | McKay et al. | 514/401 |
| 2009/0281663 | A1 * | 11/2009 | Robida | 700/265 |
| 2010/0112032 | A1 * | 5/2010 | Guelcher et al. | 424/423 |

FOREIGN PATENT DOCUMENTS

| | | |
|---|---|---|
| DE | 41 31 562 A1 | 3/1993 |
| DE | 10255285 | 6/2004 |
| DE | 102004005783 A1 | 12/2004 |
| EP | 0 587 106 | 3/1994 |
| EP | 0 605 497 | 7/1994 |
| EP | 1 070 509 | 1/2001 |
| EP | 1 087 752 | 4/2001 |
| EP | 1 293 245 | 3/2003 |
| EP | 1 457 483 A1 | 9/2004 |
| WO | WO 99/49716 | 10/1999 |
| WO | WO 9949716 A2 * | 10/1999 ............. A61K 9/127 |
| WO | WO 2002/09677 | 2/2002 |
| WO | WO 2003/030945 | 4/2003 |

OTHER PUBLICATIONS

Micciche et al. The combination of reducing agents/iron as environmentally friendlier alternatives for Co-based driers in the drying of alkyd paints. Progress in Organic Coatings 53 (2005) 99-105.*
Fundamentals of Dairy Chemistry, $3^{rd}$ ed, chapter 1. Noble Wong ed, Aspen Publishers (Maryland) 1999.*
Eppendorf. Eppendorf safe-lock tube 2.0 mL. Retrieved May 1, 2013 from: http://www.eppendorf.com/int/index.php?pb=b1165adb1285c7e5&action=products&contentid=1&catalognode=9775&productpage=3.*
Jenness, Robert et al. Fundamentals of Dairy Chemistry—Composition of Milk. 1999. Aspen Publishers, Inc. Third Edition. pp. 1-5.*
Al-Mehdi, A.B. et al., "A phospholipase $A_2$, inhibitor decreases generation of thiobarbituric acid reactive substance during lung ischemia-reperfusion," *BBA* 1167: 56-62 (1993).
Benita, S. et al., "Submicron emulsions as colloidal drug carriers for intravenous administration: comprehensive physicochemical characterization," *J. Pharm. Sci.* 82: 1069-1079 (1993).
Huwyler, J. et al., "Brain drug delivery of small molecules using immunoliposomes," *Proc. Natl. Acad. Sci. USA* 93:14164-14169 (1996).
Lasch, J. et al, Preparation of Liposomes; in "Liposomes—a practical approach;" Torchilin, V.P. and Weissig, V., Ed., 2nd edition (2003).
Lucks, J.S. et al., "Parenterale fettemulsionen," *Krankenhauspharmazie* 15:51-57 (1994).
Maas, B. et al., "Stability of bendamustine hydrochloride in infusions," *Pharmazie* 49:775-777 (1994).
Macdonald, R.E. et al., "Small-volume extrusion apparatus for preparation of large, unilamellar vesicles," *BBA* 1061:297-303 (1991).
Moog, R. et al., Effect of nucleoside analogues and oligonucleotides on hydrolysis of liposomal phospholipids, *Int. J. Pharm.* 206:43-53 (2000).
Moog et al., "Change in pharmacokinetic and pharmacodynamic behavior of gemcitabine in human tumor xenografts upon entrapment in vesicular phospholipid gels," *Cancer Chem Pharmacol* 49:356 (2002).
Müller R.H. et al., Solid lipid nonaparticles (SLN)—An alternative colloidal carrier system for controlled drug delivery, *Eur. J. Pharm. Biopharm.* 41:62-69 (1995).
Müller, R.H., "Solid lipid nanoparticles—a novel drug carrier for cosmetics and pharmaceutical formulations," *Pharm. Ind.* 49:423-427 (1997).
Müller, R.H., et al., "Pharmazeutische Technologie: Moderne Arzneiformen," *Wissenschaftliche Verlagsgesellschaft* Stuttgart, 1998.
Müller, B. et al., "Impaired recycling of surfactant-like liposomes in type II pneumocytes from injured lungs," *Thorax* 58: 127-134 (2003).
Müller, R.H. et al., "SolEmuls®—novel technology for the formulation of i.v. emulsions with poorly soluble drugs," *Int. J. Pharm.* 269:293-302 (2004).
Regelin, A.E. et al., "High throughput screening method for identification of new lipofection reagents," *J. Biomol. Screening* 6(4):245-254 (2001).
Schwarz, C. et al., "Solid lipid nanoparticles (SNL) for controlled drug delivery. I. Production, characterization and sterilization," *J. Controlled Rel.* 30:83-96 (1994).
Weyhers, H. et al., "'Solid lipid nanoparticles'—determination of in vitro toxicity," *Proc. 1st world meeting APV/APGI*, Budapest, 489-490 (1995).

(56) References Cited

OTHER PUBLICATIONS

Wissel et al., "SP-A-binding protein BP55 is involved in surfactant endocytosis by type II pneumocytes," *AMJ Physiol* 271:1432-40 (1996).
Yuan, F. et al., "Mirovascular Permeability and Interstitial Penetration of Sterically Stabilized (Stealth) Liposomes in a Human Tumor Xenograft," *Cancer Res*. 54:3352-3356 (1994).
International Preliminary Report on Patentability issued by the International Bureau dated Jun. 26, 2007 for PCT/EP2005/ 057157 filed on Dec. 23, 2005 and published as WO 2006/069985 on Jun. 7, 2006 (Applicant—KTB Tumorforschungsgesellschaft mbH // Inventors—Massing et al.) (1 page).
International Search Report on Patentability issued by the International Bureau dated Jun. 27, 2006 for PCT/EP2005/057157 filed on Dec. 23, 2005 and published as WO 2006/069985 on Jun. 7, 2006 (Applicant—KTB Tumorforschungsgesellschaft mbH // Inventors—Massing et al.) (11 pages).
Written Opinion issued by the International Bureau dated Jun. 27, 2006 for PCT/EP2005/057157 filed on Dec. 23, 2005 and published as WO 2006/069985 on Jun. 7, 2006 (Applicant—KTB Tumorforschungsgesellschaft mbH // Inventors—Massing et al.) (11 pages).
European Search Report dated May 11, 2005 for EP App. No. 04106939.4, filed on Dec. 23, 2004 (Applicant—KTB Tumorforschungsgesellschaft mbH // Inventors—Massing et al.).
European Search Report dated Nov. 30, 2011 for EP App. No. 10178676.2, filed on Dec. 23, 2005 (Applicant—KTB Tumorforschungsgesellschaft mbH // Inventors—Massing et al.).

\* cited by examiner

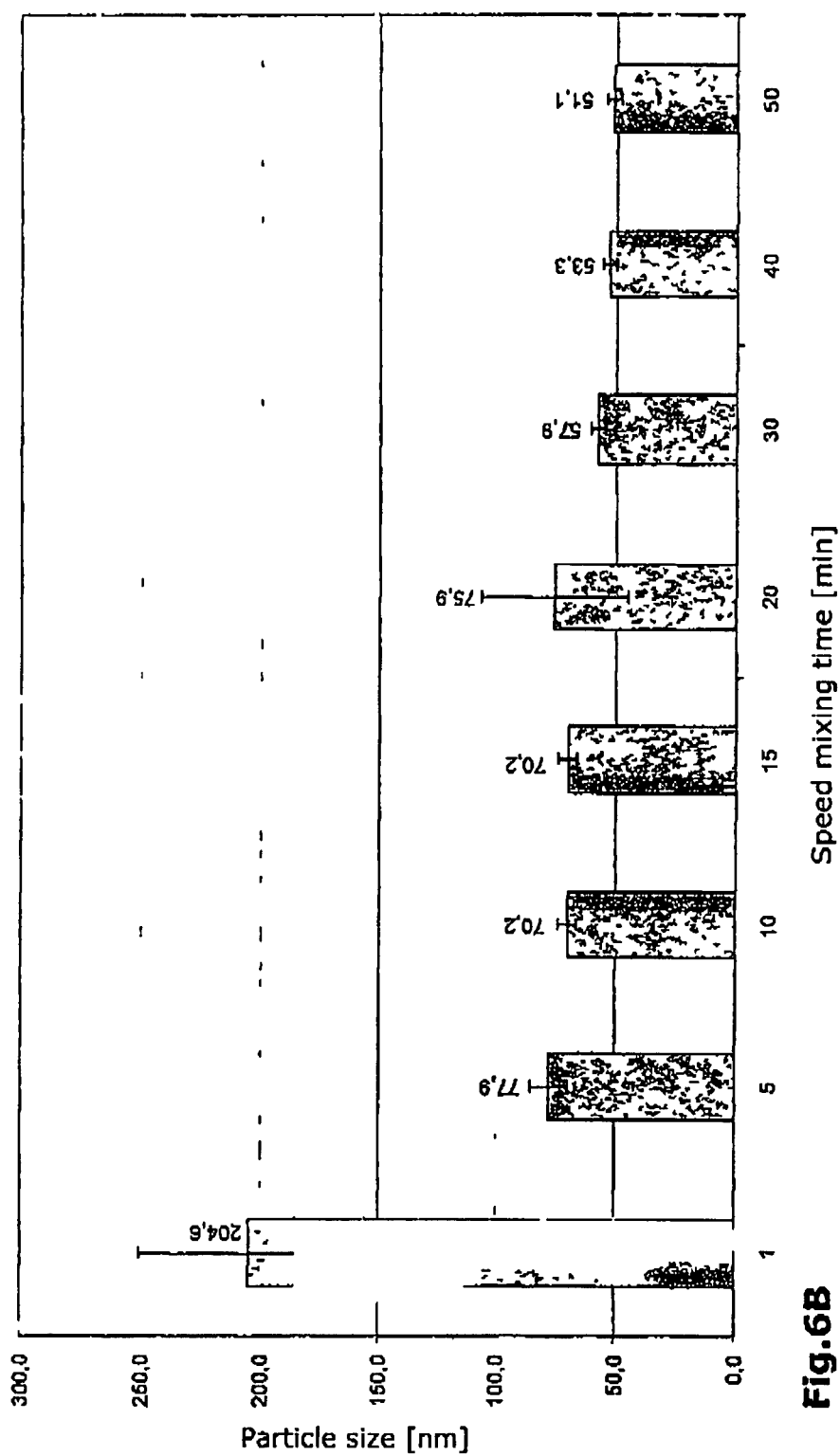

MANUFACTURE OF LIPID-BASED NANOPARTICLES USING A DUAL ASYMMETRIC CENTRIFUGE

CROSS REFERENCE TO RELATED APPLICATIONS

The present application is a National Phase Application of International Application No. PCT/EP2005/0057157, filed Dec. 23, 2005, which claims priority to European Patent Application No. 04106939.4 filed Dec. 23, 2004, which applications are incorporated herein fully by this reference.

The invention pertains to a process for manufacturing lipid-based nanoparticles with the use of a dual asymmetric centrifuge, products obtained by said process, kits for manufacturing said nanoparticles using a dual asymmetric centrifuge and accessory for carrying out said process.

BACKGROUND OF THE INVENTION

Lipid-based nanoparticles such as, e.g., liposomes, nano- and microemulsions, SLN (solid lipid nanoparticles), nanocapsules, nanospheres and lipoplexes are important auxiliaries for a multitude of technical processes and medical applications.

Liposomes are spherical entities consisting of lipides. In aqueous solutions liposomes are formed by a self-aggregation of said lipides with the formation of a lipid double layer, said lipid double layer enclosing an aqueous interior space.

Depending on physical parameters such as mechanical effects, pressure, temperature and the ion concentration and the present lipides and auxiliaries, unilamellar, oligolamellar or multilamellar liposomes are formed. Depending on the components thereof, said liposomes may carry a positive or negative excess charge.

Liposomes may also be loaded with substances which, depending on the lipophilia or hydrophilicity thereof, are predominantly enclosed in the lipid layer or predominantly enclosed in the aqueous interior of the liposomes. Such liposomes are used in diagnostic detection processes, as therapeutic agents for transporting active substances within the organism or as an active substance depot. In addition, said liposomes may also be used in the biological and biomedical research and in plant protection (e.g., for the transport of substances into cells). Also a use in cosmetics is possible.

The properties of liposomes such as, e.g., the stability or storability thereof, essentially depend on the substances existing in the lipid layer.

For the manufacturing of liposomes, membrane-forming lipids such as, e.g., phosphatidylcholine, phsophatidylglycerol, phosphatidylserine, phosphatidylinositol and phosphatidylethanolamine, sphingomyelin, cationic lipides such as, e.g., DOTAP, DC-Chol, DOTMA, Inter alia, membrane-forming amphiphiles such as, e.g., block polymers, alkyl esters, alkyl ethers, alkyl amides of sugars, diols and polyols, amines, amino acids, peptides and sugars and cholesterol and other substances are used.

For the manufacturing of empty or substance-loaded liposomes being as uniform as possible various processes are known. These processes have been reviewed by Lasch et al. in a concise manner (Lasch, J. et al, Preparation of Liposomes; in "Liposomes—a practical approach", Torchilin, V. P. and Weissig, V., Ed., 2nd edition (2003)).

Many manufacturing processes start from so-called "hand-shaken vesicles" which may be formed by a simple rehydration of a lipid film and a subsequent shaking (In most cases in a flask). In most cases, said liposomes are very non-uniform with respect to the size and the lamellarity thereof. The liposome size may be standardized (usually reduced in size) and the lamellarity of said liposomes may be reduced using processes such as extrusion, the freeze-thaw method or ultrasonication:

Extrusion processes use an extruder and usually enable the manufacturing of only small amounts (manual extrusion) (Macdonald, R. E. et al., BBA 1061:297-303 (1991)). The manufacturing of large amounts involves high expenditures in equipment (pump, membranes etc.) and a cumbersome processing. Moreover, only low-viscosity media can be extruded resulting in a low inclusion efficiency. Due to the open manipulation of media, the preparation of sterile samples is cumbersome, and with radioactive substances there is a danger of a contamination of the environment. Moreover, prior to extrusion and hydration lipid mixtures have to be produced by a common dissolution and a subsequent evaporation.

Although injection processes and detergent processes are possible in industrial scale, the removal of solvents and detergents is problematic. High lipid concentrations cannot be obtained in a simple way, and the excess of aqueous media allows only low inclusion efficiencies to be achieved with hydrophilic substances.

Also freeze-thaw steps may standardize the size of non-uniform, often multilamellar liposomes and lower the lamellarity thereof. In most cases, an increased inclusion efficiency for water-soluble substances arises.

With the above-mentioned processes in particular the low enclosing efficiency for hydrophilic substances is a problem inherent in the system. The reason for this is that said processes can be carried out with only low lipid amounts and consequently the formed liposomes can enclose only a low portion of the aqueous total volume. Consequently, only low amounts of hydrophilic substances dissolved in the aqueous phase will be enclosed.

The enclosing efficiency may be increased, e.g., by a liposome manufacturing using high-pressure homogenization since considerably larger lipid amounts may be used in this case. As a result, a so-called liposome gel having a very high lipid content is obtained, wherein the aqueous outer volume approximately corresponds with the aqueous inner volume with respect to the order of magnitude. Then, the content of the enclosed hydrophilic active substance is correspondingly high. Another advantage is the possibility to manufacture high formulation amounts which is easily achieved using high-pressure homogenization. Moreover, the high pressure homogenization is advantageous in that it produces especially small vesicles which are especially interesting in the medial field, e.g., for a tumour targeting using the so-called EPR effect (enhanced permeability and retention). This effect is based on the vascular permeability of blood vessels in tumours which is strongly increased in most cases. Due to the leakiness of the vessels, small particles such as, e.g., liposomes (in particular if they are very small) may leave the vascular bed and enrich in the tumour (Yuan, F. et al., Cancer Res. 54:3352-3356 (1994)).

The economically especially advantageous properties of high-pressure homogenization (small vesicles, high enclosure efficiency, high sample amounts) is connected with a number of drawbacks:

The manufacturing of sterile materials absolutely essential for the use in humans and animals is problematic. Although a sterile manufacturing is possible, it is cumbersome since the necessary high-pressure homogenization has to be performed under clean-room conditions or the material has to be autoclaved subsequently. Moreover, autoclaving vesicular phospholipid gels (VPG) containing active substances often poses problems with the stability of active substances and/or lipides (Moog, R. et al., Int. J. Pharm. 206:43-53 (2000)).

With the use of high-pressure homogenization it is especially difficult to produce small sample amounts required, e.g., in medical or molecular-biological laboratories (if only a small sample amount is available, if radioactive substances are used etc.) or in the screening of a very large number of different lipid formulations (e.g., in the field of preformulation).

Moreover, the homogenization step heavily strains the sample which is critical with expensive and sensitive substances such as, e.g. biological materials (DNA, siRNA, antibodies, peptides, proteins) or with sensitive low-molecular substances such as, e.g., antioxidants, lipids containing specific highly unsaturated fatty acids, cytostatics (alkylating agents etc.).

The equipment required for high-pressure homogenization is expensive, bulky and unacceptable for many (in particular medical/molecular-biological) laboratories. Since each composition change requires the machine to be cleaned, the sample throughput is low; a screening of different mixtures is practically impossible and can be automated only with difficulties (e.g., in the field of preformulations).

Moreover, an outstanding technological know-how is required, not least to limit the danger for the environment resulting from the use of hazardous substances (e.g., radioactive substances or cytostatics).

The problems encountered in the manufacturing of liposomes have already resulted in the use of liposome gels for cosmetic purposes, said gels being formed only by a rehydration of a lipid mixture with a standardization of the vesicles being totally dispensed with (DE 10255285). Such formulations are not suitable for use in pharmacy, biomedicine and medicine and at least critical for use in cosmetics due to a low reproducibility of the vesicle composition.

SLN are nanoparticles having a size of from about 50 to 1000 nm. A review of SLN is given in Pharmazeutische Technologie. Moderne Arzneiformen. R. H. Müller und G. E. Hildebrand, Wissenschaftliche Verlagsgesellschaft Stuttgart, 1998. Contrary to emulsions, the matrix material consists of solid lipides. Here, physiological lipides (e.g., corresponding triglycerides) or lipides from physiological components (e.g., glycerides from endogenic fatty acids) are predominantly used. It is supposed that this achieves a good in vivo compatibility (Weyhers, H. et al., Proc. 1st world meeting APV/APGI, Budapest, 489-490 (1995)). However, the matrix material is not restricted to physiological lipids, also waxes and non-physiological triglycerides being conceivable.

To date, SLN have been manufactured by high-pressure homogenization of water-dispersed lipides in molten or solid states (hot or cold homogenization, see Müller, R. H., Pharm. Ind. 49; 423-427 (1997); EP 0 605 497; Schwarz, C. et al., J. Controlled Rel. 30:83-96 (1994); Müller R. H. et al., Eur. J. Pharm. Biopharm. 41:62-69 (1995)). This manufacturing technique by high-pressure homogenization is characterized in that the SLN size is very homogenous and, moreover, the amount of microparticles is very low. However, as in the manufacturing of liposomes, the expenditure for said high-pressure homogenization is very high.

Another type of lipid-based nanoparticles are droplets in emulsions, with submicron emulsions (SME) being meant here, that is, O/W emulsions having droplet/particle sizes below 1 µm (Benita, S. et al., J. Pharm. Sci. 82: 1069-1079 (1993)). So-called nanoemulsions having droplet sizes of from 50 to 1000 nm cannot be limited therefrom.

Said emulsions have been used in the parenteral feeding for a long time (Lucks, J. S. et al., Krankenhauspharmazie 15:51-57 (1994)), however, they may also be used as excipient. A review covering SME is found in Pharmazeutische Technologie: Moderne Arzneiformen. R. H. Müller und G. E. Hildebrand, Wissenschaftliche Verlagsgesellschaft Stuttgart, 1998.

Among the SME manufacturing processes used today, the high-pressure homogenization (using piston gap homogenizers or a microfluidizer technique) is the leading technique. In the laboratory or pilot plant scale, also ultrasonic homogenization is used mainly because high-pressure homogenization is too tedious.

WO 02/09677 describes the manufacturing of a dispersion comprising a O/W or W/O emulsion and an active substance sparingly soluble in oil and water (amphotericine B). Said dispersion may contain an amount of the active substance exceeding the amount obtained by adding the maximum solubility in water or oil. However, homogenization is high-energetically, that is, by high-pressure homogenization accompanied by the above-mentioned drawbacks. Said process has also been described as the so-called SolEmuls technology (Müller, R. H. et al., Int. 3. Pharm. 269:293-302 (2004)). Here, by using high-energy high pressure homogenization sparingly soluble active substances such as carbamazepin, itraconazoles or amphotericine B are incorporated into emulsions by co-homogenization which results in a strong increase in particular of the dissolution speed but also has the above-mentioned drawbacks of a high pressure homogenization.

Hence, the problem addressed by the invention was to provide a process for the manufacturing of lipid-based nanoparticles kept as simple as possible, said process being milder and safer than high pressure homogenization, suited for screening and enabling the manufacturing of nanoparticles also and in particular in the laboratory scale.

BRIEF DESCRIPTION OF THE INVENTION

It has been found that a dual asymmetric centrifuge is very well suited for the manufacturing of lipid-based nanoparticles, wherein said nanoparticles may be loaded with one or more physiologically active and/or diagnostically/biologically/chemically/biochemically relevant compound(s).

Hence, the invention pertains to
(1) a process for manufacturing lipid-based nanoparticles by homogenizing a lipid component with an aqueous component and/or by incorporating compounds in preformed lipid-based nanoparticles in a dual asymmetric centrifuge (DAC);
(2) a preferred embodiment of process (1), wherein
 (i) said homogenization and/or incorporating is performed with at least 200 rpm, preferably at least 1000 rpm and maximally 4000 rpm, especially preferred at from 2000 to 3540 rpm, most preferred at from 2500 to 3540 rpm; and/or
 (ii) the g-number is at least 1.2 g, preferably at least 80 g, especially preferred at least 300 g, particularly preferred from 550 to 1000 g or from 620 to 1500 g; and/or
 (iii) the counter-rotation ratio is from 1:6 to 6:1, preferably below 5:1, especially preferred below 3:1; and/or
 (iv) the centrifugation time is from 30 s to 1 h, preferably from 1 to 30 min, especially preferred from 3 to 20 min; and/or (v) a mixing aid, preferably glass beads having a diameter of from 0.5 to 6 mm is used;

(3) a preferred embodiment of process (1) or (2), wherein the lipid-based nanoparticles are liposomes including vesicular phospholipid gels (VPG);

(4) a preferred embodiment of process (1) or (2), wherein the lipid-based nanoparticles are solid nanoparticles (SLN);

(5) a preferred embodiment of process (1) or (2), wherein the lipid-based nanoparticles are droplets in emulsions;

(6) a preferred embodiment of processes (1) to (5) suited for the screening of lipid-based nanoparticles which were preferably manufactured according to the process of one of embodiments (1) to (5) in the field of preformulation;

(7) lipid-based nanoparticles manufacturable or manufactured according to processes (1) to (5) which preferably contain sensitive or short-life substances which are especially preferably selected from active substances sensitive to hydrolysis and short-life diagnostic agents;

(8) the use of the lipid-based nanoparticles according to embodiment (7) for manufacturing pharmaceutical, cosmetic, diagnostic compositions and compositions useful in plant protection or as food stuff;

(9) a kit for performing the process according to embodiment (1) to (6);

(10) a mixing device for chemical and/or biological substances, in particular a DAC suited for performing processes (1) to (6) having a first driving device (12) for rotating a cantilever (16) around a first rotation axis (18), a mixing vessel (40) for taking up the substances connected with the cantilever (16) spaced apart from first rotation axis (18) and a second driving device (30) for rotating the mixing vessel (40) around a second rotation axis (28) extending through the mixing vessel (40)

characterized in that interior walls (46) of the mixing device (40) have different distances to the second rotation axis (28);

(11) a mixing vessel for a DAZ, in particular for performing process (1) to (6) and/or for the mixing device (10) having a first uptake space (50) for taking up a first substance and at least one second uptake space (52) for taking up a second substance, characterized in that in a separating wall (70) between the uptake spaces (50, 52) an opening (68) is provided to enable a transfer of one of the substances into the other uptake space (50, 52) in the presence of centrifugal forces;

(12) the use of the mixing device and/or the mixing vessel according to embodiment (10) or (11) for intermixing single-phase or multi-phase mixtures, for the disruption of cells and for working up tissues in a dual asymmetric centrifuge;

(13) a mixing device for a DAC, in particular for performing the process according to (1) to (6), suited for taking up injection bottles;

(14) a process for crushing solid matter, in particular for disrupting cells or tissue, comprising the treatment of said solid matter in a DAC;

(15) a composition, in particular a pharmaceutical or diagnostic composition, comprising the lipid-based nanoparticles (7); and

(16) a kit for performing the process according to (14) comprising the holding device (88).

BRIEF DESCRIPTION OF THE FIGURES

Referring to the following figures, the invention will be described in more detail in the detailed description of the invention.

DETAILED DESCRIPTION OF THE INVENTION

Figure 1:
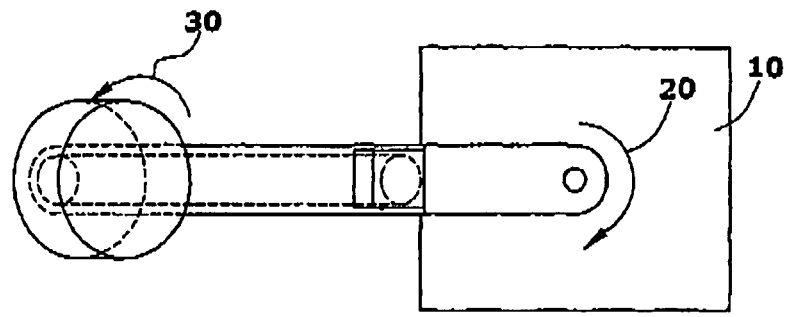
FIG. 1: top view of the schematic design of a dual asymmetric centrifuge

The process of the invention has proven to be a surprisingly simple technique for manufacturing liposomal dispersions, vesicular phospholipid gels and other lipid-based nanoparticles which either do not contain an active substance or which contain at least one physiologically effective and/or diagnostic compound as an active substance. In particular, the technology of the invention enables a sterile manufacture of said particles in one step and, if desired, also the loading thereof with various substances, said technique also enabling the manufacture of small, but also large amounts. Contrary to the state of the art, the technique can be performed in a very simple and rapid way and enables also persons lacking liposome/nanoparticle know-how the manufacture thereof. Due to the rapid practicability of the process, also instable substances (e.g., substances sensible to hydrolysis) may be enclosed in lipid-based nanoparticles. Since the manufacturing proceeds sterile and very fast, the nanoparticles may be used for the manufacture of pharmaceuticals, e.g., of injections, also and especially directly prior to the administration to patients ("bedside preparation"). Lipid-based nanoparticles having different sizes may be manufactures by changing the parameters of the dual asymmetric centrifuge (e.g., centrifugation time and speed). It is possible to include both large and small molecules and much more. It was especially surprising that comparable to the manufacture of liposomes using high-pressure homogenization only very small amounts of particles having diameters >1 μm are formed in the inventive manufacture of liposomes and other nanoparticles, which does not comprise an extrusion step and thus enables the formulations to be used in the i.v. (intravenous) administration. Due to the minimum diameter of a blood capillary (5-6 µm), the diameter of the largest administered particles has to be distinctly below 5 µm in such cases since otherwise an embolism may result. The smaller the number of particles having particle diameters >1 µm is, the more advantageous this is for clinical application.

It is surprising that the process of the invention allows the manufacture of liposomes having a size distribution corresponding to the size distribution of liposomes obtained by high-pressure homogenization (cf. FIG. 5) and that said liposomes may be loaded with the same efficiency as the latter. In addition, further drawbacks of the high-pressure homogenization process, in particular the high stress of the sample, the low sample throughput, the required relatively high sample volumes, the need of special know-how and the difficulties encountered during sterile processing and the handling of hazardous substances are solved.

In the following, some of the used terms will be defined in greater detail:

"Lipid-based nanoparticles" within the meaning of the present invention are nanoparticles having particle sizes of 1 µm at most which consist of at least one lipid component and optionally contain an aqueous component and/or additional compounds, in particular active substances, or may be loaded therewith. Lipid-based nanoparticles may exist as solid substance of dispersed in an aqueous component. Preferably, they are liposomes, SLN or emulsion droplets (SME).

A "lipid component" within the meaning of the invention comprises one or more compounds selected from the group comprising amphiphiles, lipids and/or detergents. Preferably, it comprises at least one compound selected from phospholipids, glycolipids, cholesterols, sphingolipids, polyethylene glycol lipid derivatives, cationic lipids, triglycerides and waxes. Examples 3 and 4 for liposomes, example 15 for SLN and example 14 for emulsions demonstrate how different the lipids used in the process according to (1) may be.

When using a mixture of several lipids as lipid component, said mixture may be employed as a solid mixture or as a mixture of single lipid crystals. Labelled lipids may be introduced for analytical purposes in biological, medical and chemical tests. Fluorescence labelled, spin-labelled or radiolabelled lipids are preferred.

The multitude of possible combinations in the selection of the parts of the lipid component for forming lipid-based nanoparticles enables the skilled person the tailored design of said particles. As mere examples, immunoliposomes having specific antibodies on the surface thereof, negatively charged liposomes for RES targeting, positively charged liposomes for targeting activated endothel and neutral liposomes for the passive enrichment in tumour tissue by the EPR effect may be mentioned.

Within the context of the invention, the "aqueous component" is water or an aqueous alcoholic and/or buffer-containing solution. In addition, salts and other low-molecular water-soluble substances may be dissolved therein. Hereinafter, it will be designated as "aqueous phase" or "aqueous medium".

A "solvent" is a liquid which can dissolve gases, other liquids or solid matter without chemical reactions between dissolved matter and dissolving liquid taking place.

"Physiologically active compounds" (hereinafter also designated as "active substances") within the meaning of the present invention are compounds which may induce a physiologic reaction in living beings, especially in the plant, human or animal. In particular, said compounds include the active substances used in cosmetics, plant protection and therapy.

A "liposome gel" within the meaning of the present invention is a liposomal formulation which is viscous, i.e., no longer free-flowing, due to a high content of lipid components and thus has a high liposome (vesicle) density. A liposome gel preferably contains more than 20% of the lipid component, especially preferred membrane-forming amphiphiles, exceptionally preferred more than 30% of membrane-forming amphiphiles. A liposome gel has to be differentiated from liposome-containing gels where the gel properties (viscosity, prevention of free flowing) are not caused by a high liposome density but by a gel-forming component such as, e.g., polyacrylamide.

A "vesicular phospholipid gel" (VPG) is a liposome gel wherein the amphiphiles used for the formation of vesicles consist of phospholipids to a certain amount, preferably at least 30%. In the literature, vesicular phospholipid gels (VPG) are often designated as liposome gels since nearly all known liposome gels are VPG.

"Passive loading" (EP 1087752) denotes a process wherein a prefabricated liposomal formulation which is preferably a liposome gel and especially preferred a VPG is mixed with an active substance which may diffuse through liposome membranes with the active substance initially being inserted between the liposomes. Due to a subsequent incubation proceeding at room temperature, however, preferably at a slightly raised temperature, especially preferred at 40-80° C., the active substance diffuses into the liposomes until an equilibrium has formed between the active substance amounts within and outside the liposomes. The prefabricated liposomal formulation may be manufactured, e.g., using high-pressure homogenization or the process employing a DAC as presented here. Important active substances where the passive loading may be used are, e.g., gemicitabines, vincristine, vindesin and platinum compounds used in cancer therapy.

"Solid lipid nanoparticles" (SLN), also designated as "solid lipid nanoparticles", are nanoparticles in the size range of from 10 to 1000 nm (if a nanoparticle must not have a size of 1000 nm by definition, "up to 1000 nm" means "up to 1000 nm", that is, less than 1000 nm in this context), preferably of from 20 to 400 nm, wherein—contrary to emulsions—the matrix material consists of solid lipides (completely lipophilic lipids). Physiologically compatible lipids, corresponding triglycerides or also waxes are predominantly used as solid lipids. However, also non-physiological lipids may be used. Depending on the lipophilia thereof, active substances incorporated in SLN are either dissolved in the lipid matrix (solid solution) or dispersed in the matrix. Usually, SLN in aqueous dispersions are stabilized by surfactants, however, also a surfactant-free manufacture is possible. SLN may be formulated both as aqueous dispersions and as dry products (lyophilization or spray-drying).

A "lipoplex" is a lipid-nucleic acid complex, in particular a lipid-DNA or lipid-RNA complex and consists of at least one lipid component (preferably an amphiphil) with the hydrophilic portion of the lipid component carrying a positive charge under the conditions of lipoplex formation, and a nucleic acid component carrying a negative charge under the conditions of lipoplex formation. Depending on the composition, the mean charge of a lipoplex may be positive, negative or also neutral. A positive charge is preferred. Above all, lipoplexes are used for the transfer of nucleic acids into cells. In this case a positive charge of the lipoplex is helpful to allow the lipoplex to bind to the normally negatively charged cell wall and to be taken up from there. Special lipoplex forms are, e.g., AVE (artificial virus-like envelopes) where the nucleic acid initially condensates (e.g., with a positively charged polymer) and subsequently is enclosed in liposomes.

Within the context of the present invention, "mean size" designates the median of the vesicle size, i.e., the vesicle diameter where 50% of the vesicles are smaller and 50% of the vesicles are larger than the stated value. Usually, this corresponds to the maximum of a Gaussian size distribution.

Within the context of the present invention, the "enclosure efficiency" is the ratio (percentage) of the amount of the measured substance (e.g., of an active substance) which is included in the lipid-based nanoparticles, associated to the nanoparticles or incorporated into the nanoparticles, to the total amount of the respective substance used for the formulation.

A "dual asymmetric centrifuge" (DAC) is a centrifuge where in addition to the processes of a classic centrifugation the vessel containing the material to be centrifuged is preferably rotated opposite to the direction of rotation, e.g., with a fourth to a third of the centrifuge speed. This results in a constant mixing of the material introduced into the DAC. The high centripetal force also enables viscous masses to be mixed (EP 1293245). In this process a strong inner friction is generated in particular in viscous masses. Usually, the DAC is used for mixing pastes with pastes, pastes with powders, powders with powders etc. Typical application areas are the mixing of sealants and coating agents (such as, e.g., silicones, polyurethanes and acrylates), lacquers, inks and pigments and the mixing of one-, two- or multi-component products in liquid or paste-like forms.

The dual asymmetric centrifuge used in the process according to embodiment (1) to (7) and in the use (12) of the invention is hereinafter described in more detail with reference to FIG. 1 and FIG. 2. It features a housing or base body 10. Within the housing 10 a first driving device 12 in the form of an electric motor is provided. The first driving device 12 drives a drive shaft 14. The drive shaft 14 is connected to a cantilever 16 which may consequently rotate around a first rotation axis 18 with the aid of the first driving device. Thus, the first driving device 12 rotates the preferably angled cantilever 16, e.g., in the direction of an arrow 20.

Spaced apart from the rotation axis 18, a vessel 24 is provided at one end 22 of the cantilever 16. The vessel 24 is rotatably connected to the shaft 26 by the cantilever 16. Hence, the vessel 24 is rotatable around a second rotation axis 28, e.g., in the direction of an arrow 30. A second driving device 30 is provided to drive the vessel 24, said driving device being attached, e.g., to the cantilever 16. In order to reduce the impact of centrifugal forces on the second driving device 30, said second driving device is located as close as possible at the first rotation axis 18. Then, the drive is effected by a V-belt and two corresponding pulleys 34, 36 connected with the shaft 26 or a motor shaft 38.

The simultaneous turning of the vessel 24 around both of the rotation axes 18 and 28 results in a mixing of the substances provided in the vessel 24. This ensures a high mixing homogeneity. Preferably, both rotation axes 18, 28 are not only arranged in a spaced-apart manner but also at an angle to each other. Said angle may be provided by an angled cantilever 16. It is also possible to arrange the rotation axis 28 at an angle to the cantilever. The angle between both rotation axes 18, 28 is preferably in the range of from 0 to 70°, especially preferred of from 30 to 70°.

The "counter-rotation ratio" designates the ratio of full revolutions around both rotation axes 18, 28 of a DAC, resp. Said ratio is the number of revolutions the main rotor 16 has to perform around the rotation axis 18 to achieve one revolution of the vessel container 16 around the rotation axis 28. Correspondingly, the counter-rotation ratio is given as XX:1, and it is positive if the sample vessel 24 turns contrary to the main turning arm 16.

The speed of the cantilever is preferably at least 200 rpm and 4000 rpm at most. Preferably, it is in the range of from 2000-3540 rpm. The speed of the vessel 24 around the rotation axis 28 is preferably adjusted such that a counter-rotation ratio of from 1:6 to 6:1 is achieved. Preferably, it is at least one fifth, especially preferred by at least one third of the speed of the cantilever 16, which corresponds to a counter-rotation ratio of 5:1 and 3.1, resp. Moreover, the directions of rotation 20, 30 are preferably opposite to each other.

In a suitable holder also containers or mixing vessels, in particular injection vials, glass containers or plastic containers such as, e.g., Eppendorf vessels, may be inserted in the vessel 24. Then, the vessel 24 serves as a receptacle. The process of embodiment (1) enables most various vessels to be used. Vessels made from glass or plastics having diameters from 5-75 mm, especially preferred from 9-75 mm are preferred. In addition to commercially available injection vials, in particular Eppendorf vessels having diameters from 9 to 10 mm and glass vessels having diameters of from 9 to 40 mm are preferred. Further suitable special vessels to be used in embodiment (1) are the special mixing vessels of embodiments (10) and (11) exemplarily described in FIGS. 3 and 4. Also the use of tubes and syringes as mixing vessels is possible.

In order to improve mixing further, mixing aids (synonymous terms: dispersing aid, homogenizing aid) may be provided within the vessel 24 or within the containers arranged therein. Said mixing aids may be a defined roughness within the inner wall of the vessel 24/the container. Web-shaped mixing aids may also be arranged within the vessel 24/the container. Vessels having roughened, knopped or corrugated inner surfaces are preferred. Moreover, glass beads in various amounts and sizes, blades on the inner vessel wall or a suitably formed central and/or circumferential vessel insert may also be mixing aids. Especially preferred mixing aids are beads made from substances such as alloy steel, agate, zirconia, tungsten carbide, teflon, teflon having a steel core, polyamide, sinter corundum, silicon nitride and glass. Glass beads and steel beads, particularly glass beads are exceptionally preferred. The preferred diameter of said beads is a diameter of at least 0.4 mm, especially preferred of from 0.5 to 6 mm.

Within the context of the present invention, "speed mixing" means the use of a Speedmixer® or another DAC, preferably a type DAC 150 FVZ Speedmixer® of the company Hauschild GmbH und Co KG having a counter-rotation ratio of approximately 2.8:1 or 4.2:1, especially preferred 4.2:1, or a dual asymmetric centrifuge having a similar counter-rotation ratio.

In the processes (1) or (2) of the invention and the use (12) of the invention batch sizes of few milligrams up to 3000 g (3 kg) are possible with batch sizes of from 5 mg to 150 g, exceptionally preferred of from 20 mg to 40 g being preferred.

The process according to (1) or (2) is preferably performed using a DAC suited for taking-up reaction vessels having a size of from 0.1 to 110 ml, preferably of from 0.1 to 25 ml, especially preferred of from 0.5 to 10 ml, exceptionally preferred of from 0.5 to 2 ml.

In the processes according to (1) and (2), a centrifugal force of at least 1.2 g, preferably at least 80 g, especially preferred at least 300 g, exceptionally preferred at least 550 to 1000 g or from 620 to 1500 g is applied on the substances to be mixed and arranged in the vessel 24. However, the maximum centrifugal force may be up to 3000 g, preferably up to 2500 g.

Figure 7:
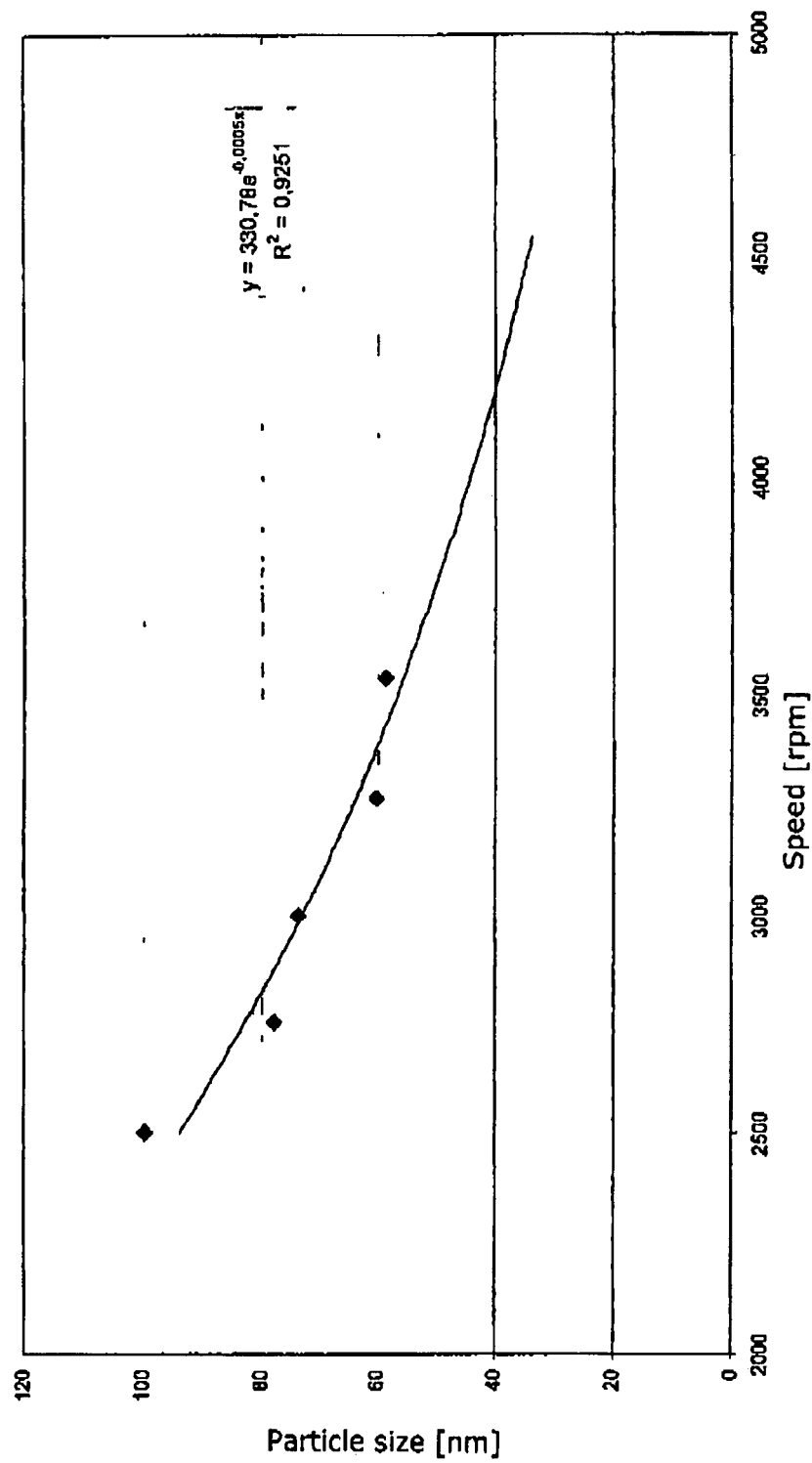

Inter alia, the vesicle size of the nanoparticles depends on the DAC speed. The higher the speed (in rpm) or the g number is, the smaller the obtainable vesicle sizes are. Relevant speeds for the manufacturing in particular of small vesicles having diameters below 100 nm are in the range exceeding 2000 rpm. Particle sizes in the range of a 30 nm diameter should be achievable by increasing the speed further, presumably to a speed of from 4000 to 5000 rpm (FIG. 7).

In a particularly preferred aspect, the homogenization in the process of embodiment (2) is performed at 3540 rpm and/or at 550 to 1000 g. In an especially preferred aspect, the counter-rotation ratio in the process according to (2) is below or equal to 4.2:1, exceptionally preferred below or equal to 2.8:1, the centrifugation time is from 30 s to 1 h, preferably from 1 to 40 min, especially preferred from 3 to 30 min, exceptionally preferred from 3 to 20 min.

A possible aspect of embodiments (2) and (12) is the use of a Speedmixe® as double asymmetric centrifuge, especially preferred of a type DAC 150 FVZ Speedmixer® of the company Hauschild GmbH und Co KG having a counter-rotation ratio of approximately 2.8:1 or 4.2:1, especially preferred 4.2:1.

In the process according to (1) or (2) the lipid component preferably comprises one or several amphiphiles, lipids, detergents, especially preferred at least one lipid selected from phospholipids, glycolipids, cholesterols, sphingolipids, polyethylene glycol lipid derivatives, cationic lipids, triglycerides and waxes. Preferably, the aqueous component is water or an aqueous alcoholic and/or buffer containing solution. One or both of the components may contain one or several functional substances being lipophilic or hydrophilic. Said substances are preferably selected from the group of active substances and diagnostically or biosynthetically compounds or compounds relevant for the chemical synthesis. Moreover, detergents and/or emulsifiers may be added as adjuvants.

The process of the embodiments (1) and (2) may be used for manufacturing lipid-based nanoparticles containing either at least one active substance and/or a substance relevant in diagnostics or chemical synthesis or which are empty (hence, which do not contain such a substance).

The process according to embodiment (1) may be performed as follows: the lipids (and optionally adjuvants) contemplated for the respective formulation and optionally one or several active substance(s) are added to a suitable vessel (mixing vessel) in the dry state, subsequently the aqueous component optionally containing one or several active substance(s) and further adjuvants is added, and the mixture is "speed-mixed". A corresponding (lipid) mixture optionally containing one or several active substance(s) present as a solid solution may directly be employed as lipid component. Alternatively, the addition of the aqueous component may be performed in a metered manner during homogenization in the DAC. Also charging the aqueous component and adding the lipid component, optionally in a suited solvent, is possible.

If lipid mixtures are used, said mixtures may be employed as single components or ready-mixed lipid mixtures ("solid solutions", that is, mixed crystals made from the separate lipids) in the process according to (1) (Example 3). In both cases lipid-based nanoparticles are obtained.

Due to the high inner friction in the speedmix process and the strongly increased contact events between the particles being formed and the substances to be enclosed, process (1) forms nanoparticles loaded with active substances in a short time. If the amount of the added aqueous component is kept low (resulting in relatively high lipid concentrations), a viscous lipid paste consisting of nanoparticles is formed, said paste being known, e.g., from WO 96/005808 for liposome gels. In specific cases, this approach is advantageous in that—due to the high lipid concentration and hence a strong inner friction—small particles are formed especially efficiently and in the case of liposomes an especially high enclosure efficiency for water-soluble substances may be achieved (high amount of enclosed aqueous phase). Optionally, subsequently to the vesicle formation non-enclosed active substance may be separated off. If additional aqueous medium is added after the vesicle formation and a speed-mixing is performed for a short time, the formed highly concentrated dispersion is redispersed (diluted). Hence, in the case of liposomes a normal liposomal dispersion still having a high enclosure efficiency is formed.

Hence, the present invention also comprises the dilution of an already preformulated dispersion of lipid-based nanoparticles, preferably of a liposome dispersion, especially preferred of a VPG by incorporating an (additional) aqueous component within the nanoparticles using a DAC (redispersion). Then, the lipid-based nanoparticies may already contain one or several active substance(s). Also a redispersion of cremes and dispersions with solid particles, in particular $SiO_2$ particles, is possible (example 9). Here, the aqueous medium is added either in one step or in several steps directly to the existing dispersion of lipid-based nanoparticles or applied using a mixing vessel of embodiment (11) during speed mixing. Especially preferred, this process of the invention may be used for redispersing VPG containing gemcitabines (manufactured by high pressure homogenization and a subsequent passive loading) to obtain an injectable liposomal dispersion (example 9).

The process of the invention allows a simple sterile working: only the filling of the mixture components into sterile vessels has to be performed under sterile conditions. After sealing the vessels, speed mixing may be performed in nonsterile rooms. Moreover, also the use of dangerous substances, in particular of cytostatics, radioactive compounds (in particular of radioactive lipids and active substances) for manufacturing said nanoparticles is possible in a comparatively safe manner since the substances exist in sealed vessels during the mixing procedure. Hence, when using said process the danger of contamination for humans and machines is very low.

The inventive processes (1) and (2) may achieve high enclosure efficiencies. Moreover, the inventive process enables a mild treatment of the sample and may considerably reduce the formation of unwanted constituents. Thus, a containing gemcitabine using the DAC technique with that of the manufacture of comparable liposomes by passive loading employing high pressure homogenization shows a significant lower amount of lyso-PC with the use of the DAC technique (example 5D).

With regard to the use of a mixing aid, the centrifugation speed, the diameter of the used vessel, the centrifugation time and the temperature, the inventive process according to (1) and (2) is variable and is thus suited for the purposive manufacture of lipid-based nanoparticles having various particle sizes and in various amounts (cf. examples 1 and 2). Preferably, said nanoparticles have particles sizes of from 5 to 1000 nm, especially preferred of from 15 to 200 nm, exceptionally preferred of from 20 to 150 nm. If a nanoparticle must not have a size of 1000 nm by definition, "up to 1000 nm" means "up to 1000 nm", that is, less than 1000 nm in this context. Varying the variable parameters, different liposomal formulations may purposively be manufactured as required from one and the same starting lipid mixture. Moreover, it is possible to speed-mix also in vessels having small diameters. Hence, also standard laboratory vessels such as Eppendorf® vessels etc. may be used for a screening or for tasks in the field of molecular biology. In particular with an increase of the DAC centrifugation speed and/or a decrease of the counter-rotation ratio with small vessel diameters, an important reduction of vesicle sizes and a decrease of the required centrifugation time may be expected.

Figure 5A:
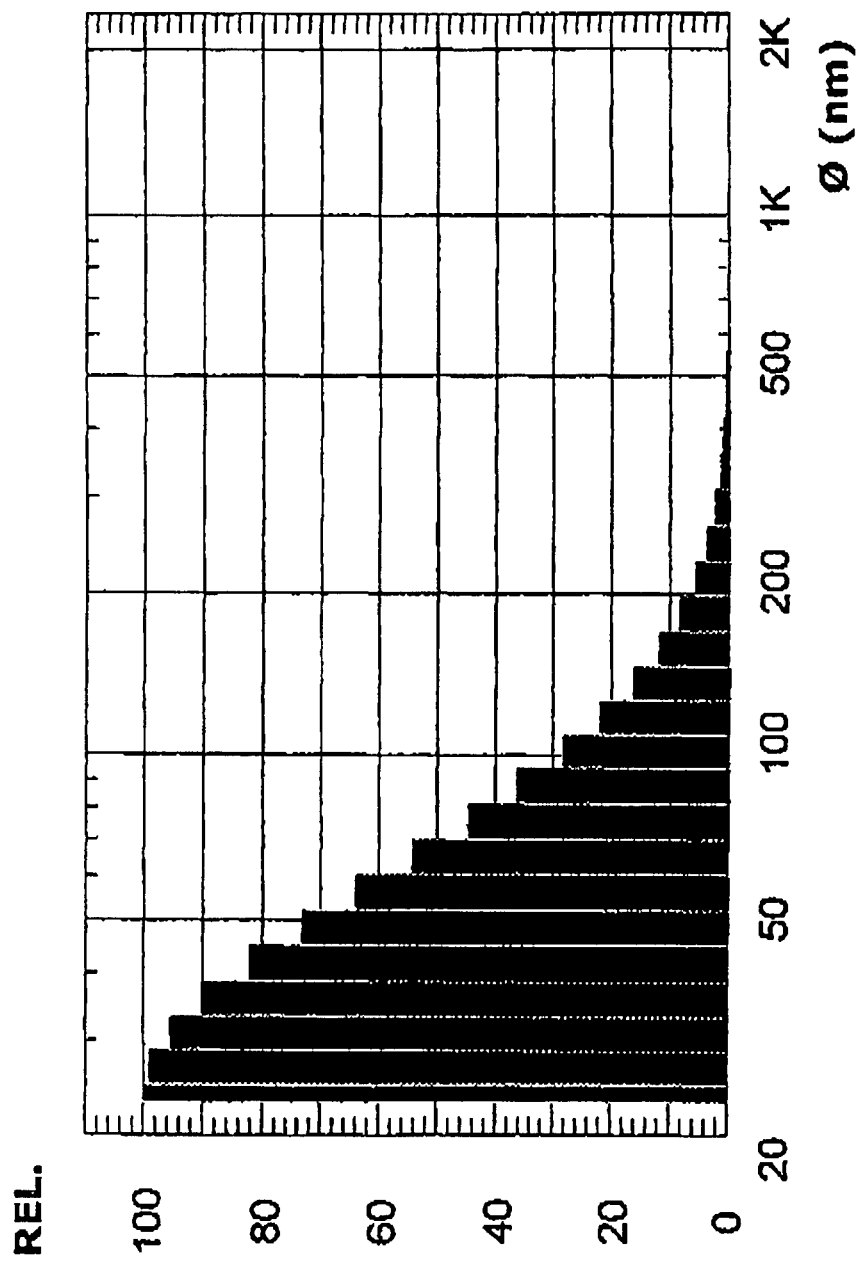
FIG. 5; particle size distribution of liposomes (example 1, vials 2 and 3), determined as relative Gaussian distribution based on the number of particles; Diam: vesicle diameter; Rel: relative amount in %: a) manufactured using a DAC (vial 2) and b) manufactured by high-pressure homogenization (vial 3)
Figure 5B:
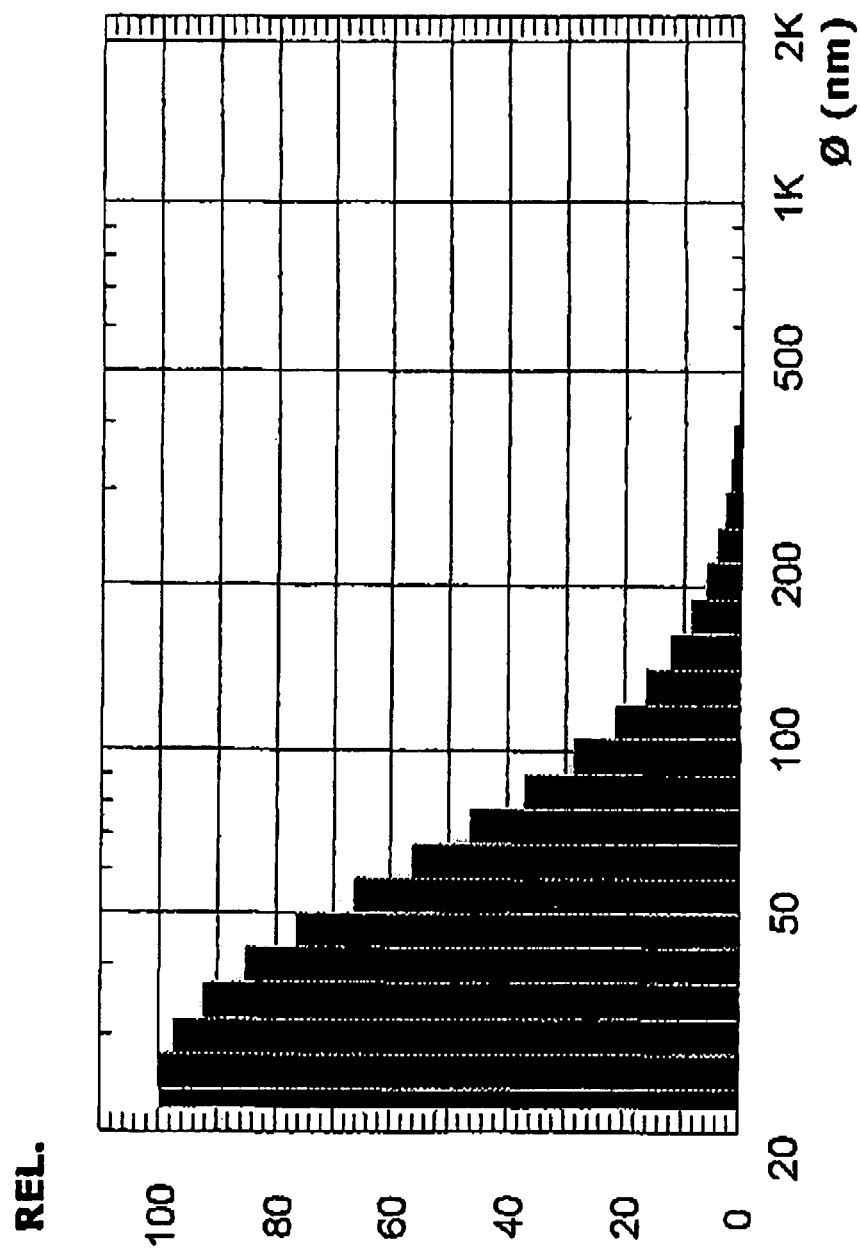

Using the process of the invention, liposome gels and (after redispersion) liposomal dispersions having properties comparable to those of comparatively composed liposome gels and dispersions from high pressure homogenization may be obtained (example 1, FIG. 5). Due to the low number of particles having sizes >1 µm, products manufactured according to the inventive process are suited for parenteral administration (see example 1, Nutriflex® as a comparison).

For manufacturing liposomes of embodiment (3), membrane-forming lipids (also designated as amphiphiles) are used as lipid components. The nature thereof (synthetically or isolated from natural sources) is irrelevant for the use thereof in the invention. Phospholipids, cholesterol and cationic lipids, above all phosphatidylcholine, phosphatidylglycerol, phosphatidylserine, phosphatidylinositol, phosphatidylethanolamine and sphingomyeline are especially preferred. Phosphatidylcholine is exceptionally preferred (Examples 1 to 9, 11, 13, 16). The fatty acid hydrocarbon chains of phospholipides may be saturated or unsaturated and have the same or different lengths with chain lengths of C12 to C20 being preferred and chain lengths of C14 to C18 being especially preferred. The selection of phospholipides having specific fatty acid compositions is relevant, e.g., for the formation of thermosensitive liposomes. In the membranes thereof, liposomes may also contain so-called lyso phospholipids differing from phospholipids by the omission of one fatty acid in the sn 2 position. Other phospholipids preferably used to form liposomes are ceramides, kardiolipin, tetraetherlipids and ether phospholipids. In the latter one or two phospholipid ester bonds are substituted by ether bonds. The combination of DOPE and CHEMS has been proved efficient in the formation of pH sensitive liposomes. Liposomes which may be degraded especially fast by sPLA2 consist of, e.g., phosphatidylcholine, a stealth component (as a protection from RES uptake) and a negatively charged phospholipid.

Also commercially available phospholipid mixtures or fractions of such mixtures may be used. One example is the so-called lecithin which has to contain at least 20% of phosphatidylcholine.

Cholesterol is a particularly important lipid component for the formation of liposomes.

Also the so-called stealth components protecting liposomes against uptake by RES cells may be used as lipid component. Said stealth components may be, e.g., phospholipides having polyethylene glycol chains or polyglcerols at the polar end thereof.

Also functionalized lipids serving to bind, e.g., proteins or peptides to liposomes (coupling lipids) may be employed. Thiol-reactive maleimide groups bonded to membrane-forming lipid components by PEG spacers with various lengths may serve as an example. Also non-covalent bonding principles are a factor, with avidine groups bonded to membrane-forming lipid components being one example.

Also membrane-forming lipids having chemical structures with biological functions at the hydrophilic end thereof are possible lipid components. Examples for such chemical structures are specific peptide sequences (e.g., for bonding to cells) or folic acid (for bonding to the folic acid receptor).

Moreover, other membrane-forming amphiphiles such as, e.g., block polymers, alkyl esters, alkyl ethers, alkyl amides of sugars, diols and polyols, amines, amino acids, peptides and sugars and cholesterol may be used as lipid components.

Moreover, cationic lipids are often used as a lipid component in the manufacture of liposomes. Said cationic lipids may be DOTAP, DOTMA, DC-Chol, DOSPER, DMRIE, DAC-30, DOGS, DORI, SpdC, SAINTS or also structures described in EP 03 005 513.1 and the N,N,N-trialkylamino-2,3-propandiols (WO 03/030945). Important non-cationic lipid components in the manufacturing of cationic liposomes are DOPE and cholesterol.

For the manufacture of liposomes according to embodiment (3) the lipid mixture may be selected such that the liposomes become pH sensitive (e.g., by DOPE/CHEMS (cholesterol hemisuccinate) mixtures) or sensitive to high temperatures (temperature-sensitive liposomes). The mixture may also be selected such that the liposomes may be degraded by PLA2 especially fast (PLA2 sensitive liposomes).

Moreover, liposomes may be sterically stabilized, e.g., by incorporating PEG chain containing lipids or lipids carrying polyglycerols as head group. Thus, liposomes can be protected against an excessive uptake by cells of the RES (reticulo-endothelial system).

Also lipid components carrying a fluorescence marker or a spin label in the lipophilic portion or in the hydrophilic portion thereof or lipids having a radioactive labelling may be incorporated.

Liposomes of embodiment (3) may be neutral, anionic or cationic (table 3). Independent of the charge, they may be loaded with one and the same active substance (example 5C) enabling the transport of the latter to various target regions of a cell or a tissue of a human or animal body, organ or tissue, a plant or a plant portion or a reaction mixture. Liposomes with cationic lipids (e.g., DOTAP) especially preferably binding to activated endothel (e.g., tumour endothelins), negatively charged liposomes binding to RES and neutral liposomes which may incorporate in tumour tissue by the EPR effect or which, as a systemic depot, may protect active substances in the body against a fast decomposition thereof are especially interesting. Moreover, the mentioned liposomes may be used as a local depot for a slow release of active substances in the body.

Moreover, lipids enabling additional substances to be bonded to the liposomes may be used. These are in particular so-called coupling lipids enabling, e.g., antibodies, antibody fragments and other proteins, but also peptides to be bonded to the liposome surface. Here, the bonding may be chemical (e.g., by maleimide groups at the coupling lipids and thiol groups at the antibody/protein/peptide). The reactive groups may also be bonded to the lipids by longer spacers (e.g., PEG chains). Moreover, the bonding of substances to the liposome surface may be affected by non-covalent principles such as, e.g., by the avidine-streptavidine-coupling.

Lipids already carrying specific peptides or molecules enabling a bonding to specific cells or epitopes in the polar head thereof (e.g., folic acid-carrying lipids; bonding to folic acid receptor) are especially interesting.

Using RNAse-free lipids is advantageous for enclosing RNA.

The lipid component concentration in the liposomes according to (3) is from 1 to 600 mM, preferably from 20 to 600 mM, especially preferred from 200 to 600 mM.

The following compounds may be enclosed by liposomes according to embodiment (3) (example 5):

proteins (e.g., hemoglobin, albumin; example 5A)

vitamins (e.g., tocopherol) and antioxidants enzymes (e.g. luciferase) and enzyme inhibitors (e.g., sPLA2-inhibitor, example 4C)

cytokines nucleic acids, above all RNA (example 5C), DNA, plasmid DNA, antisense DNA and antisense RNA, siRNA, dsRNA peptides (e.g., PSA peptides)

viruses (e.g., oncolytic viruses)

cyclodextrines including those containing active substances cell or tissue lysates and fractions thereof tumour lysates and fractions thereof magnetic nanoparticles ions, ATP, salts (e.g., copper salts)

$SiO_2$ particles (example 5F), e.g., for cremes radioactive substances, fluorescence-labelled substances (example 4B)

low-molecular compounds (e.g., trypan blue; example 5B)

active substances and diagnostics, i.a. antiestrogens, antibiotics, analgetics, antirheumatics, antiallergics, antibiotics (i.a. amphotericine B, cyclosporine, buparvaquone and atovaqouone), antiinfectives, anti-parasitic and antiinflammatory active substances, chemotherapeutics, anti-epileptics, antimycotics, corticoids, dermatics, diagnostics, hemostypics, antihemorrhagics, hypnotics, sedatives, hormones, peptides, hormone inhibitors, immunotherapeutics, cytokines, local anesthetics, migraine analgesics, narcotics, ophthalmics, psychopharmaceuticals, thyroid pharmaceuticals, sera, immunoglobulines, vaccines, metastasis inhibitors, proteins, prostaglandines, proteinkinase inhibitors and other inhibitors of important cellular signal paths (in particular in the tumour processes), metallocens, cytostatics, lipid-active substance conjugates; preferred active substances are antibiotics (above all, anthracyclines), antiparasitics, cytostatics, antiinflammatory agents, antiinfectives and substances usually not allowing the manufacture of shelf stable liposomes.

Preferably, the enclosure into liposomes is effected by adding the compounds existing in an aqueous solution/dispersion to a lipid (mixture) and subsequently employing process (1) or (2). Irrespective of the physical properties thereof, the compounds may be enclosed fast and with high efficiency.

The inventive process (1) is preferably used for enclosing active substances in liposomes.

The inventive processes (1) and (2) are particularly suited for enclosing sensible and/or short-life substances in liposomes which do normally not permit a manufacture of storage-stable liposomes or substances having a negative impact on the stability of the lipid component. Said substances include mainly:

compounds and active substances sensible to hydrolysis, preferably alkylating agents including bendamustine (example 5E), cyclophosphamide, mafosamide and platinum compounds such as cis-platinum or oxaliplatin short-life substances such as radioactively labelled compounds used in diagnostics or compounds used in positron emission tomography (PET) diagnostics.

substances which easily diffuse through (liposome) membranes and therefore are often enclosed by passive loading within liposomes, which, however, are as such instable in this process or induce an instability of the lipid component, including the cytostatics gemcitabine (example 5D), vincristine, vindesign, vinblastine, 1-β-D-arabinofuranosylcytosine (Ara-C).

To date, compounds sensible to hydrolysis are commercialized only lyophilized but not as a liposomal formulation. A substantial aspect of the invention is the use of cytostatics sensible to hydrolysis which do normally not allow the manufacture of liposomal formulations, said cytostatics including alkylating agents, platinum compounds, bendamustine and mafosamide. The fast manufacture of nanoparticles according to the invention and the gentle (clinic) redispersion ensures that also these active substances may be incorporated in a dispersion.

Furthermore, the process according to (1) and (2) is suited to incorporate active substances very fast, effectively and uniformly into a prefabricated liposome gel such as, e.g., a VPG or SLN and thus may be used to incorporate water-insoluble active substances and to prepare passive loading (cf. example 6, example 8). Of the water-insoluble active substances, amphothericine B is preferred.

Up to the present, the incorporation of active ingredients as a prerequisite for passive loading was effected by shaking the VPG mass with the active substance solution or by agitating with a stirrer or spatula (EP 1087752). The aim of the incorporation is a distribution of the active substance between the vesicles as uniform as possible. This incorporation step is critical in that it should be performed under sterile conditions since after the incorporation of the active substance into the VPG a sterilization step usually is not performed (or, with the use of gemcitabine as active substance, it must not be performed since gemcitabine catalyses the phospholipid hydrolysis under autoclaving conditions). Also by shaking the active substance may uniformly be distributed in the VPG; this is advantageous in that this can be performed in the closed vessel and thus in a sterile manner. This requires the use of a shaking aid (e.g., glass beads) which is already added during the addition of VPG to the vessel. The shaking procedure may then be effected in a laboratory shaker (e.g., Mikrodismembrator type, Braun Melsungen). However, the device requires a long time and is annoying for the laboratory/pharmacy/ward staff due to the noise emission thereof. Moreover, the procedure should be monitored since due to moved masses shakers easily "migrate" and may fall off the table.

Contrary to this, the inventive incorporation by passive loading is advantageous in that the incorporation proceeds comparatively fast (example 8). Hence, it is very gentle and timesaving at the same time.

Consequently, one aspect of the process according to (3) is the incorporation of active substances in prefabricated VPG for preparing passive loading. It is suited for the manufacture of active substance-containing VPG for clinical applications, pre-clinical tests (e.g., animal experiments) and in vitro tests (biological or biophysical; stability tests). The process is also suited for screenings wherein an active substance/lipid component combination especially suited for an application or an optimal ratio between lipid component and active substance is to be elaborated. Moreover, the process may be performed under sterile conditions which are above all necessary for the manufacture of active substance-containing VPG in the investigation of living organisms. In particular, this process may be used for the incorporation of sensible active ingredients into lipid vesicles, above all of gemcitabine, vincristine, vindesin and platinum compounds (see above). Then, the active substances may be used in a solid or dissolved state, the use as a solution being preferred.

Active substance-containing liposomes are often manufactured by the so-called injection method (injection technique) since this process may be performed in industrial scale. This method is especially advantageous if lipophilic active substances which commonly insert in or bind to the liposome membrane are to be enclosed by liposomes. In the injection process, a solution of the lipid component (and optionally also of the active substance) in an organic solvent (preferably ethanol or diethyl ether) is "injected" into a well-stirred aqueous phase. Due to the required stirring, also in the laboratory often a slightly larger scale, with the use of aqueous volumes a scale of at least 10 ml, is used. In order to be able to use the injection method also for screening, e.g., suitable active substance/lipid component combinations, carrying out said method in the millilitre scale and less would be desirable. This is achieved by applying process (1). Thereto, the mixing vessel of embodiment (11) is used. In this process, the aqueous solution is in one of the chambers, the organic solvent with the lipid component is in a second chamber. During speed mixing, the volume of the upper chamber is pressed into the lower chamber due to the centrifugal forces in the DAC. Hence, in a configuration corresponding to the classic injection method and wherein the organic solvent is injected into the aqueous phase, e.g., liposomes are thus formed (example 11C). Interestingly, this process may also be carried out in a reversed manner, i.e., by injecting the aqueous phase into the organic phase. When adding a low amount of the aqueous phase during speed mixing using the multi-chamber system, a viscous formulation is initially formed. When adding additional aqueous phase and repeating speed mixing, a uniform liposomal formulation is obtained (example 11A).

However, the injection method may be performed without applicator or a multi-chamber system of embodiment (11). For this, the aqueous phase is added to the organic phase containing the lipid component in small steps and subjected to speed mixing in between (example 11B). This initially results in a viscous and finally, after the complete addition of the aqueous phase, a uniform liposomal dispersion having vesicle sizes comparable to the use of a mixing vessel of embodiment (11) (example 11A). Above all, the injection method is particularly suited for screenings, especially for the enclosure of lipophilic substances in liposomes and in small batch sizes and/or in an automated manner.

The process according to embodiment (1), the mixing device according to (10) and the mixing vessel according to (11) may also be used to redisperse and/or dilute already manufactures lipid-based nanoparticles or particle-containing mixtures. This also applies to viscous mixtures and mixtures containing solid particles (example 9). In this case, the addition of the diluting medium may optionally be effected directly or with the aid of an applicator. Preferably, a mixing vessel like in embodiment (11) or a comparably designed mixing vessel is used as applicator. This aspect of the invention is significant in particular for the preparation of active substance-containing VPG (e.g., VPG containing gemcitabine or vincristine) for administration (e.g., in the patient). In this case an injectable formulation is usually needed requiring the VPG formulation to be redispersed/diluted. This is easily achieved by the process described here and is distinctly advantageous over the shaking process employed to date with respect to the speed of performance, process safety and simplicity.

The redispersion of the invention is of significance in particular also for $SiO_2$ dispersions. Traditionally, silica dispersions have been used in the prophylaxis of brittle fingernails and hair, in the strengthening of connective tissue and in various other applications. Here, a typical formulation is, e.g., a dispersion of from 2 to 3 g of silicic acid anhydride/100 ml water. The silica crystals present in such formulations tend to aggregate which may inter alia be demonstrated by the fact that a size determination of a silica dispersion suspended in water by photon correlation spectroscopy (PCS) is not possible due to the existing large particles. The process according to (1) may be used to separate the obviously formed non-covalent aggregates from silica particles.

Surprisingly, the process according to (1) is even suitable for improving high-pressure homogenization. In order to manufacture VPG and other dispersions by high-pressure homogenization, the lipids/lipid mixtures or other substances are previously usually rehydrated/stirred with the required amount of aqueous medium. During this simple mixing of substance/lipid and aqueous medium a homogenous dispersion is not formed. For this reason the first cycles of high-pressure homogenization often proceed non-uniformly. Only after approximately three cycles the mixture seems to be homogenous. A distinct simplification and also improvement of the high-pressure homogenization process may be achieved if the substance or the mixture of the lipid and the aqueous medium is treated in a DAC prior to high-pressure homogenization and is thus homogenous already at the beginning of high-pressure homogenization. This enables the process to be accelerated, and at least the first cycles may be dispensed with. This was shown exemplarily by manufacturing a VPG (example 13).

For embodiments (1), (2), (3), (7), (8) and (15) of the invention, VPG are especially preferred lipid-based nano-particles.

The SLN obtainable by the process according to embodiment (4) consist of at least one solid lipid, preferably a triglyceride or wax, and in a preferred aspect additionally of at least one emulsifier/stabilizer or surfactant. For the manufacture according to (4), in principle the solid lipid and optionally a suitable emulsifier/stabilizer are heated in a relatively low amount of the aqueous component to a suitable temperature. Said temperature is the temperature where the solid lipid exists in liquid form and the emulsifier/stabilizer can deploy its emulsifying properties. Preferably, this temperature exceeds room temperature. The formed, preferably viscous mixture is speed-mixed. After the desired SLN dispersion has formed, the SLN dispersion is adjusted to a desired concentration by adding further aqueous component and applying a short speed-mixing and kept at low temperatures until the SLN harden (example 15). In the manufacturing of SLN lipids being solid at room temperature are used, and the amount of lipid component is usually high. This requires the SLN to be manufactured at temperatures which preferably at least correspond to the melting temperature of the lipid component and thus usually exceed room temperature.

Examples for Lipids Suited for the Manufacture of SLN which are Solid at Room Temperature Carnauba wax, hydroxyoctacosanylhydroxy stearate, Chinese wax, cetyl palmitate, beeswax and similar waxes. Additional examples for solid lipids are C20-40 di- and triglycerides having saturated and unsaturated fatty acids, C20-40 fatty alcohols, C20-40 fatty amines and the compounds thereof and sterols.

Examples of Detergents/Surfactants/Emulsifiers/Stabilizers in SLN

Lecithins, polyethoxysorbitan ester (Tween® types), such as, e.g., laurate (Tween® 20/21), palmitate (Tween® 40), stearate (Tween® 60/61), tristearate (Tween® 65), oleate (Tween® 80/81) or trioleate (Tween® 85), sodium glycolate and sodium lauryl sulfate (SDS) and the sorbitan fatty esters (Span types) and TritonX® 100.

Sterically stabilizing substances such as poloxamers and poloxamine, ethoxylated sorbitan fatty ester, in particular polysorbates (e.g., polysorbate 80 corresponding to Tween® 80), ethoxylated mono and diglycerides, ethoxylated lipids, ethoxylated fatty alcohols or fatty acids, ethers and esters of sugars or of sugar alcohols with fatty acids or fatty alcohols (e.g., saccharose(di) stearate, laurate, octanoate, palmitate, myristate).

Alcohols and alcohol derivatives having lipophilic regions, such as, e.g., tyloxapol.

Charged ionic stabilizers such as diacetylphosphate, phosphatidylglycerol, lecithins of different origin (e.g. egg or soy lecithin), chemically modified lecithins (e.g., hydrogenated lecithins), synthesized lecithins as well as phospholipids and sphingomyelins, a mixture of lecithins with phospholipids, sterols (e.g., cholesterol and cholesterol derivatives, stigmasterine) and also saturated and unsaturated fatty acids, sodium cholate, sodium glycocholate, sodium taurocholate, sodium desoxycholate or mixtures thereof, zwitterionic surfactants such as, e.g., CHAPSO or CHAPS and cationic surfactants such as benzyldimethylhexadecyl ammonium chloride or cetyl pyridinium chloride.

Emulsifiers being active substances at the same time, in particular the lung surfactant tyloxapole, are especially preferred as a component of the lipid component.

Active substances suited for the inventive incorporation into SLN and/or the inventive manufacturing of SLN containing active substances are preferably water-insoluble active substances and active substances which may be dispersed or dissolved in the solid lipid matrix (slow release formulation). Especially preferred water-insoluble active substances are taxanes, amphotericine B, campthotecine and dekapeptides such as Cetrorelix®.

In principle, the process for manufacturing emulsions (SME) according to embodiment (5) may be carried out according to both of the following procedures (example 14); in the first procedure, all required components, typically a lipid component (e.g., a triglyceride oil), en emulsifier and an aqueous component, are added to a suitable vessel and the mixture is speed-mixed. Preferably, a dispersing aid, in particular glass beads, is used. The desired emulsion is formed after few minutes (example 14A). In the second procedure, the lipid component and the emulsifier(s) and a low amount of the aqueous component are combined and speed-mixed preferably together with a dispersing aid. Then, emulsions having small droplet diameters are formed also with the use of a low amount of emulsifier. The emulsion is adjusted to the required concentration by adding additional aqueous component and additional speed mixing (example 14B). Both processes may be performed at temperatures exceeding room temperature.

Emulsions manufactured by the process according to embodiment (5) preferably contain from 10-20% of oil and are stabilized by 0.5-2.5% of lecithin, preferably egg or soy lecithin. Said SME may be stabilized by polymer emulsifiers instead of lecithin. Such emulsifiers are often advantageous as to their higher chemical stability and their increased tolerance against electrolytes.

Examples for polymer emulsifiers are: proteins such as, e.g., albumin, casein or gelatin, protein derivatives such as collagen hydrolysate surfactants, cellulose ethers such as methylcellulose or methylhydroxypropylcellulose (MHPC), polysiloxane polyalkyl polyether copolymers, natural polysaccharides such as, e.g., gum arabic, polyoxyethylene polyoxypropylene block copolymers such as the poloxamers or the polyacrylate polyalkylacrylate crosspolymers such as the pemulenes.

Preferred oils as the lipid component for inventive emulsions are selected from the group consisting of soy oil, olive oil, safflower oil (thistle oil) and other plant oils, long-chain triglycerides (LCT), middle-chain triglycerides (MCT) such as, e.g., miglyols, fish oils and oils having increased amounts of unsaturated fatty acids, acetylated partial glycerides like in Stesolid®. Said oils may be used singly or as mixtures.

Active substances contained in emulsions manufactured according to (5) are preferably water-insoluble active substances. Taxanes, amphotericin B, Camphthotecin and dekapeptides such as, e.g., Cetrorelix® are especially preferred.

The process according to (1) is also suited for the manufacturing of lipoplexes. Today, lipoplexes are used for the non-viral transfer of genetic material (e.g., nucleic acids, DNA, cDNA, RNA, antisense RNA, antisense DNA, dsRNA, siRNA) into cells. This requires lipoplexes to be manufactured from lipid components consisting entirely or only partially of cationic lipids by an incubation with the genetic material. A problem with lipoplex formation is the non-uniform formation thereof which may influence both the process of transferring nucleic acids into cells and the in vivo behaviour thereof. This partially results from the initially highly different concentrations of cationic and anionic components when combining nucleic acids and the lipid component and from the very fast process of electrostatic association. This results in the formation of initial lipoplexes statistically containing too much of the nucleic acid component and others containing to much of the lipid component. Since said components obviously cannot be separated after the first bonding, the final lipoplexes are formed from said primary complexes then having highly different properties. This may also be derived from the different lipoplex sizes after the manufacturing thereof.

Hence, a process enabling a fast and homogenous mixing of the lipid and the nucleic acid component in particular in a small scale and resulting in uniform lipoplexes is needed. This may be achieved by using a process according to (1). Then, one of several approaches according to the invention may be adhered to:

When using the two-chamber system (FIG. 4) with a hole 68 between the uptake spaces 50 and 52, said hole allowing either a fast or a slow and more uniform transfer of the liquid volume from the upper into the lower chamber after starting the mixing procedure, a nucleic acid solution is added to the lower chamber and a dispersion of cationic liposomes is added to the upper chamber. After the start of the mixing process, the cationic liposomes enter the nucleic acid solution. Hence, uniform lipoplexes are formed. This process may also be performed with interchanged additions (nucleic acid in the uptake space 52, liposomes in the uptake space 50).

Figure 4:
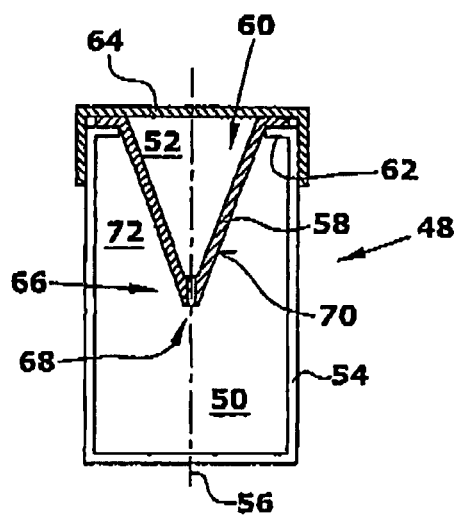
FIG. 4: mixing vessel having an opening and to uptake spaces according to embodiment (11)

When using a three-chamber system wherein the second uptake space 52 in FIG. 4 is embodied two times or separated by a separating wall resulting in two chambers and each of the chambers/uptake spaces 52 has an exit opening, the dispersions with the cationic lipids and the nucleic acid solution are filled into one of the chambers/uptake spaces 52, respectively, and the multi-chamber system is subjected to a speed mixing. This process results in a combination of both components in the lower chamber with uniform mixing, which results in uniform lipoplexes.

As nucleic acid, cDNA, siRNA or dsRNA are preferably used for the inventive manufacturing of lipoplexes.

Due to the reproducible and uniform manufacturing of lipoplexes and the possibility of sterile working, the system described here is suited in particular for clinical applications in the field of gene therapy.

The inventive process may be used for manufacturing lipid-based nanoparticles, in particular liposomes, but also emulsions and SLN without requiring specialized knowledge about the technology. In particular, this applies to the use of the kit according to embodiment (9). This is advantageous in medical, pharmaceutical and molecular-biologic laboratories where the enclosure of specific substances (e.g., proteins, antibodies, peptides, DNA, siRNA, inhibitors) in lipid-based nanoparticles is often required, e.g., for overcoming the cell membrane, but which have neither the required knowledge about the preparation and/or loading of lipid-based nanoparticles nor the required equipment. This problem may be solved by the provision of prefabricated kits according to (9) where already premanufactured lipid-based nanoparticles or suitable lipids for the inventive manufacturing of said nanoparticles are provided preferably in small vessels (e.g., Eppendorf vessels). The user only has to add a test substance (as a solution or solid substance) to the vessel, start the speed mix procedure and subsequently incubate and/or dilute the lipid-based nanoparticles by adding aqueous medium. A comparable approach is used for the manufacturing of lipid-based nanoparticles required, e.g., in technological laboratories.

The process according to (1) offers a new application range for lipid-based nanoparticles, namely the incorporation of instable, in particular active substances subject to hydrolysis and other short-life substances, in particular from the group of diagnostics immediately prior to the application thereof such as, e.g., the bedside preparation of an injection. Clinical applications of nanoparticles containing instable substances have not been known due to the low storage stability thereof. This applies in particular to liposomal formulations.

Despite their limited stability, using the process of the invention lipid-based nanoparticles may be loaded with an active substance and used for the treatment of patients. To this end, a freshly prepared active substance solution (made from a lyophilizing substance) is added to a suitable, sterile lipid component and subsequently the lipid-based nanoparticle is prepared in a DAC. Then, the formed active substance-containing nanoparticle may directly be diluted by adding a physiologically compatible medium (e.g., a 0.9% saline solution) and then administered, e.g., by transferring it into an injection bag. The time of preparing the active substance-containing liposomes is so short that a hydrolysis of the active substance will hardly occur. This process is especially suited for hydrolysis-instable cytostatics, preferably alkylating agents (e.g., 5E). However, this process may also be used with other sensitive substances, e.g., with oxidation-sensitive substances or short-life diagnostics.

The inventive process may be used in the screening (6) for suitable nanoparticles for the inclusion of active substances (e.g., for activity tests using animals or in vitro) or in the field of the development of formulations, in particular in the field of preformulation. Then, various lipid components and/or mixtures thereof are systematically employed in test series in order to identify an optimal formulation for a specific active substance. Also an optimal active substance/lipid component ratio may be determined with the use of such a screening (example 6). Moreover, a screening for adjuvants and for the optimal design of process (1) is possible. The use of inventive kits of embodiment (9) is preferred for screening.

The screening according to embodiment (6) also comprises the use of the inventive process (1) in a robot system (e.g., Tecan® Pipettierroboter Genesis 150). It comprises one or more steps for the automated manufacturing of lipid-based nanoparticles using a DAC. The injection method is especially suited for this. A preferred application of the inventive screening is the screening of lipoplexes for the transfection properties thereof according to the description in Regelin, A. E. et al., J. Biomol. Screening 6(4):245-254 (2001).

The kit according to embodiment (9) contains components for carrying out the inventive processes.

In one aspect, said components are preformed lipid-based nanoparticles, in particular liposome gels, highly concentrated emulsions or highly concentrated SLN. Their composition depends on the field of application of the kit. Thus, a kit for performing passive loading contains VPGS, whereas SLNs or emulsions may additionally be contained for screening for the uptake of the substance in lipophilic substances. Prefabricated nanoparticles within this meaning also include NanoSolve, Ultraspheres®, Cerasspheres® (Lipod GmbH, Ludwigshafen, Germany) and Supravail™ (Phares Drug Delivery AG, Switzerland).

In another aspect, said kit (9) contains at least one lipid component suitable for performing the process according to the invention for the direct inclusion of substances by means of process (1), and optionally at least one aqueous component or the non-aqueous components of said aqueous component. The components may also be contained as premixes. Such kits can be used for screening, especially in the field of preformulation, in biomedical research and for the preparation of nanoparticles for the administration of active substances within the scope of the formulation of a medicament. Especially in biomedical research, the kit may additionally contain fluorescent or radioactive compounds and lipid components.

In yet another aspect, the kit (9) contains a mixing vessel of embodiment (11) and/or is suitable for performing the injection method. In such kits, the lipid component may be contained not only as a pure substance, but also dissolved in a suitable solvent. Such a kit can be preferably used for the inclusion of lipophilic substances, especially in liposomes, further for the screening (6) in the field of preformulation and in the search for optimum combinations and/or concentration ratios of drug to lipid component.

The kit containing a mixing vessel of embodiment (11) may also be used for lipoplex preparation. Preferably, it contains a two- or three-chamber mixing vessel according to (11) in which the cationic liposomes are already contained.

However, the cationic liposomes may also be contained separately from the mixing vessel according to (11). Further, the cationic liposomes may also be prepared from the corresponding lipids (which are then contained in the kit) in situ, and the nucleic acid solution may be added in a downstream step.

Further, the kit containing a mixing vessel according to (11) can be employed even if nanoparticles that are not based on lipids are prepared or examined, but the inclusion of test substances in other matrices is to be examined. Illustratively, the inclusion of nucleic acids in cationic polymers may be mentioned.

An optional component of such kits (9) is a substances, especially an adsorbent or ion exchanger, which allows for the separation of any portion of the test substance that has not been enclosed. Further, one or more dispersing aids may also be contained.

Lipid-based nanoparticles according to embodiment (7) containing sensitive or short-lived substances are preferably liposomes and SLNs, more preferably VPGs. The sensitive or short-lived substances contained therein are preferably selected from hydrolysis-sensitive drugs and short-lived diagnostic agents. In particular, said hydrolysis-sensitive drugs are selected from alkylating agents including the nitrogen mustard compounds cyclophosphamide, mafosfamide, ifosfamide, trofosfamide, chlorambucil, melphalan, bendamustine, thiotepa, busulfan and treosulfan; from nitroso urea compounds including carmustin, lomustin, nimustin, dacarbazine, temozoliomide and procarbazine; from platinum compounds including Cisplatin, Carboplatin and Oxaliplatin; and from hydroxy urea. Preferred short-lived diagnostic agents include substances containing the radioactive isotopes technetium 99, iodine 131 and 123, indium 111, thallium 201 and gallium 67, labelled compounds for PET (positron emission tomography) and gadolinium complexes.

In addition, the lipid-based nanoparticles according to embodiment (7) preferably contain those compounds which may themselves have a hydrolytic effect on lipids, especially gemcitabines or 1-β-D-arabinofuranosylcytosine (Ara-C).

The lipid-based nanoparticles according to embodiment (7) are preferably prepared by the process according to embodiments (1) to (5), and these preferred nanoparticles can be prepared only by this method. The reason for this is the advantages of the preparation process using a DAC, because a comparably high inclusion efficiency and comparably small vesicle sizes such as those obtained when the process according to the invention is applied are achieved only by high-pressure homogenization among all other processes for the preparation of lipid-based nanoparticles. However, in contrast to processes with DAC (cf. Example 20), high-pressure homogenization cannot be used for the preparation of very small amounts. Also, the preparation rate of the DAC-produced nanoparticles is seldom reached by high-pressure homogenization. Further, sterile working and the optionally required operator protection are very complicated in high-pressure homogenization, while these may be effected easily in the process using the DAC. Above all, however, the DAC process is very mild. Illustratively, the inclusion of gemcitabine and bendamustine may be mentioned: Under high-pressure conditions, gemcitabine catalyzes the hydrolysis of phospholipids, which would lead to undesirable lysophospholipids in the thus produced lipid-based nanoparticle. Bendamustine is itself hydrolyzed under high-pressure conditions. In contrast, the lipid-based nanoparticles (7) prepared by the process (1) to (5) do not contain hydrolysis products as would be produced under high pressure. Rather, they contain a maximum of 10% of lysolipid due to the preparation method or a maximum of 10% of degradation products of sensitive compounds due to the preparation method. This means that a maximum of 10% of the sensitive or short-lived substance originally employed in the process was converted to a degradation product during the inclusion process.

It may be noted that passive loading would not be suitable either for producing the lipid-based nanoparticles of embodiment (7), because passive loading is effected at an increased temperature and thus is not mild enough for the inclusion of sensitive compounds. In addition, passive loading also produces more lysolipids as compared to the process according to the invention.

Preferred lipid-based nanoparticles according to embodiment (7) include liposomes having a high inclusion efficiency and small vesicle size. Preferred substances in these nanoparticles are hydrolysis-sensitive and lipid-hydrolyzing drugs as described above, more preferably bendamustine and gemcitabine.

If very small scales are additionally necessary, including in the molecular-biological field (inclusion of DNA, RNA, proteins or peptides) or in radioactive substances to be enclosed, these nanoparticies can be prepared by the method according to (1) to (5), but not by high-pressure homogenization. For the latter, the scales would be too low.

The use (8) comprises the preparation of formulations with lipid-based nanoparticles which are preferably taken up into particular cells/tissues or bound to such cells/tissues. This also includes the preparation of immunoliposomes, of positively charged liposomes for targeting the activated endothelium, of neutral liposomes for passive enrichment in tumor tissue by the EPR effect, or for providing a systemic or local deposition, of negatively charged liposomes for macrophage and liver/spleen cell targeting, of lipid-based nanoparticles whose lipid composition is similar to that of lipoproteins and thus allows the cell targeting and the selective transport of particular lipids, especially triglycerides, of lipid-based nanoparticles using special peptides for lysosomal escape, of nanoparticles containing nucleic acids, of nanoparticles for the vaccination especially by uptake into dendritic cells, and of nanoparticles containing a labelled lipid component for the examination of trafficking. The use also includes the use as a formulation especially for drug boosting and for oral administration. The latter is enabled by the direct loading of tetraether liposomes.

For the use (8) in cosmetics, the lipid-based nanoparticles preferably include $SiO_2$ particles.

A particular advantage of the use (8) resides in its importance to the preparation of lung therapeutics. In an inflammation of the lung or in premature infants, there is often a deficiency and/or defective composition of the pulmonary surfactant. This can be substituted. Products available on the market are fully synthetic and partially synthetic preparations or isolates from, for example, surfactant from calf lung or pig lung. In an aqueous medium, the surfactant compositions predominantly form into lamellar structures (e.g., bilayers, liposomes) which, upon instillation into the lung, spread on the lung's surface and become integrated into the pulmonary surfactant. It is also possible that the lipids or lipid vesicles are taken up by pneumocytes, which partially recycle natural surfactant from the externally added surfactant.

In order that the lipids can be quickly incorporated into the lung's surfactant layer, the introduced surfactant must be dispersed as finely as possible. This is also a precondition to as uniform as possible a distribution. Most manufacturers do not leave the fine dispersion to chance, but offer their surfactant preparations as ready dispersions, i.e., the vesicles were generated already by the manufacturer. A drawback of these preparations is their reduced keeping quality (15-18 months) because phospholipids are easily hydrolyzed in an aqueous medium (Examples: Exosurf (Glaxo Wellcome), Savanta (Abbott), Curosurf (Nycomed)). In contrast, Alveofact (BI) is offered as a dry ampoule that contains the lyophilized lipid mixture. Before the application, this mixture is rehydrated at first (i.e., addition of aqueous solvent, shaking and waiting), and then the raw dispersion is further (more finely) dispersed by repeatedly sucking it into the syringe and pressing the dispersion back into the injection bottle. The disadvantage of this tedious preparation is compensated for by an increased keeping quality of the product (here: 24 months). The kind of this dispersing technique suggests that the dispersion contains many large particles and is additionally inhomogeneous.

Thus, it was the object of the invention to provide a process which on the one hand ensures the provision of very small and homogeneous particle sizes in the lipid dispersion, but on the other hand can be performed safely and quickly and in addition allows for a long product storage time. For this object, the present invention presents at least two approaches, which can be derived from the components employed:

When dry lipid mixtures (such as Alveofact dry ampoule) are used, this mixture can be processed quickly into the required homogeneous dispersion of small particles by means of the DAC technique before it is applied (Example 10).

When the lipid-based nanoparticles are prepared de novo, there is a possibility to prepare nanoparticles similar to pulmonary surfactant, optionally charged with a tracer or drug, that are suitable for therapeutical use in the lung due to their composition and particle size (Example 4).

Further, special mixtures for inclusion in lung endothelia, especially surfactant mixtures for drug targeting via lung endothelium, can be used in the process according to the invention.

A preferred result of the use (8) are pharmaceutical or diagnostic compositions which contain the lipid-based nanoparticles according to embodiment (7). These compositions of embodiment (15) are compositions in which the lipid-based nanoparticles according to the invention function as a formulation for the pharmaceutically or diagnostically active compounds as described in the previous paragraphs.

Further fields of application of the process according to (1) in addition to the preparation of nanoparticles include the preparation of creams, ointments, pastes and other semisolid formulations of medicaments and cosmetics, tablet production, the preparation of food supplements, and the reconstitution of powdery medicaments. Thus, with respect to the preparation of creams etc., the process according to the invention including a DAC is better, more flexible (use of different vessels including upside-down-filled collapsible tubes and syringes), allows for sterile work and prevents the incorporation of air, as compared to the Unguator®, which is frequently employed today. Tablet production with the DAC process allows for granulation and is also possible in research and development with a low expenditure. Food supplements and liquid food (tube feeding) can be formulated individually, for example, in hospital pharmacies. In the reconstitution of medicaments that must be dissolved before being administered, the process according to the invention is of advantage because it enables powders to be dissolved quickly and safely without bubbles.

Embodiment (10) of the invention is a mixing device for mixing chemical and/or biological substances that can be used, in particular, for performing the processes according to the invention and also includes the redispersing of lipid-based nanoparticles. In the mixing device according to the invention, the substances are mixed, especially by an agitation of a mixing vessel, which corresponds to shaking. The mixing device has an uptake vessel for taking up the substances to be mixed. The mixing vessel is provided spaced apart from a first axis of rotation and connected with a cantilever. The cantilever is connected to a first driving means, such as an electric motor, so that the cantilever is rotated about the first axis of rotation. Thus, rotating the cantilever causes the mixing vessel to move along a circular line. Further, a second driving direction is provided for rotating the mixing vessel about a second axis of rotation. Said second axis of rotation runs at a distance from said first axis of rotation. In particular, the second axis of rotation runs through the mixing vessel. According to the invention, interior walls of the mixing vessel are provided at different distances from the second axis of rotation. When the mixing vessel is rotated about the first axis of rotation and about the second axis of rotation, this causes different and variable forces to act on the substances during the rotation. These are comparable with forces acting on substances during a shaking movement. This causes a particularly good and homogeneous mixing of the substances present in the mixing vessel.

Preferably, the mixing vessel is a cylindrical vessel. The longitudinal axis of the mixing vessel is preferably provided at an angle with respect to the second axis of rotation. This angle is not 0°. Thus, the mixing behavior of the substances can be improved further. Preferably, said angle is within a range of from 70 to 110°.

In a particularly preferred embodiment, the mixing vessel is provided within an uptake vessel. In this case, the uptake vessel may be the vessel 24 of the asymmetric centrifuge described in the present application. Thus, according to the invention, it is possible to provide a mixing vessel, for example, a cylindrical one, in a lying or slant position in an uptake vessel, which is preferably also cylindrical. For this purpose, preferably, a holding means for holding the mixing vessel in an exact position within the uptake vessel is provided within the uptake vessel.

Thus, in a particularly preferred embodiment, the mixing device according to the invention is a further development of a known dual asymmetric centrifuge as described, for example, in EP 1 293 245.

Figure 2:
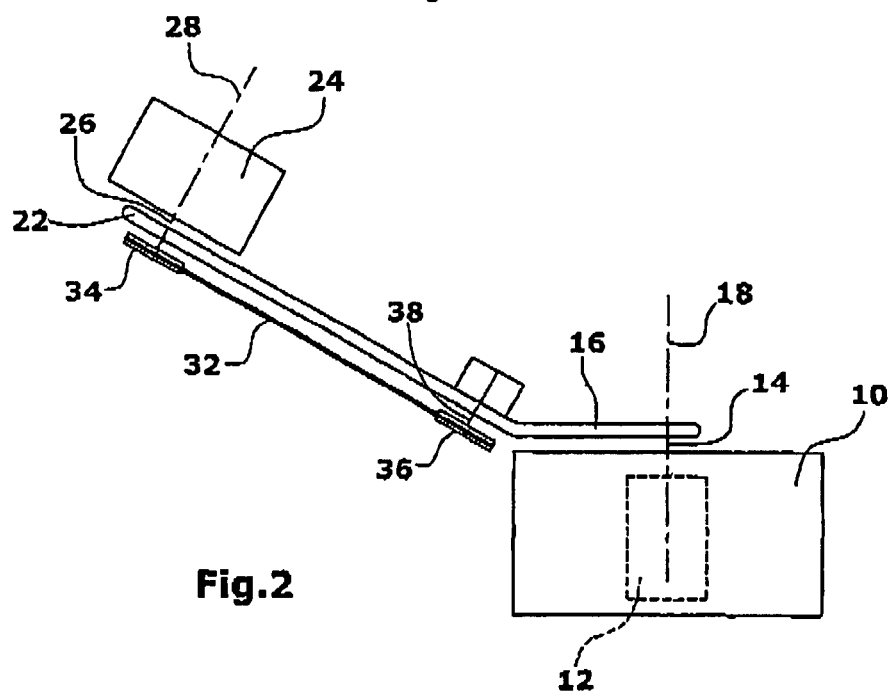
FIG. 2: side view of the schematic design of a dual asymmetric centrifuge
Figure 3:
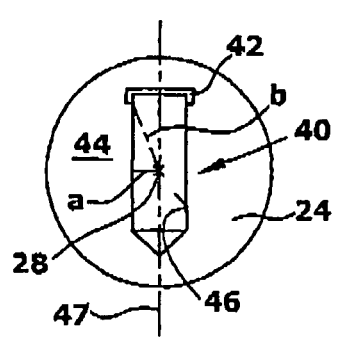
FIG. 3: mixing vessel for the mixing device according to embodiment (10)

Preferably, the mixing device of embodiment (10) has a structure as shown in FIG. 3: A mixing vessel 40 is provided within the uptake vessel 24. Said uptake vessel 24 is the vessel 24 of an asymmetrical centrifuge connected with cantilever 16 as described by means of FIGS. 1 and 2.

The mixing vessel 40 has an essentially cylindrical design and is provided in the middle of uptake vessel 24. The second axis of rotation 28 runs through the mixing vessel 40. In particular, the axis of rotation 28 essentially runs through the center of gravity of mixing vessel 40 or close to its center of gravity. Mixing vessel 40 is closed by a lid 42. In order to unequivocally define the position of mixing vessel 40 within the uptake vessel 24, a holding means 44 (not shown) is provided within the uptake vessel 24. This may be, for example, a cylindrical body made of foam or the like that has a recess into which the mixing vessel 40 can be inserted.

The mixing vessel 40 is essentially cylindrical. Preferably, the cross-section (perpendicular to the cylinder barrel) of the mixing vessel is circular, elliptical, oval or the like. It is essential that the cylinder barrel, and preferably the entire mixing vessel, does not have any corners since sample material may unintentionally accumulate in such corners. Rather, according to the invention, the interior walls of the mixing vessel preferably have a round design or are provided with rounding.

In order to ensure a good mixing of the substances within the mixing vessel 40, an interior wall 46, which is a cylinder inner wall in the Example shown, has different distances from the second axis of rotation 28. In an exemplary manner, these are outlined by dotted lines a and b.

By rotating the uptake vessel 24, variable forces act on the substances provided within the mixing vessel 40 as described by means of FIGS. 1 and 2.

In a particularly preferred embodiment (11) of the mixing vessel, which may be used, in particular, in connection with the dual asymmetric centrifuge described, first and second uptake spaces are provided. The uptake spaces serve for taking up first and second substances, respectively. According to the invention, the two uptake spaces are separated by a partition, wherein an opening is provided in said partition. Preferably, only one opening rather than several openings (such as in a sieve) is provided. The opening serves the purpose that a substance is transferred from one uptake space to the other uptake space through the opening when centrifugal forces occur. Preferably, the cross-sectional area of the opening is selected in such a way that, depending on the viscosity and the centrifugal forces occurring, the substance will pass through the opening only for centrifugal forces of more than 1.2 g, preferably more than 1.5 g. Preferably, the opening is provided in a longitudinal axis of the first and/or second uptake space. Then, preferably, the mixing vessel according to the invention is provided within a mixing device or dual asymmetric centrifuge in such a way that the centrifugal forces essentially act in the direction of the longitudinal axis, i.e., they cause the substrate to pass through the opening.

Preferably, the second uptake space is provided within the first uptake space and has a conical design, in particular. In this case, it is particularly preferred that the opening is provided at the apex of the cone. The first uptake hollow space may be a cylindrical body. The mixing vessel is preferably designed to be rotationally symmetrical to a longitudinal axis. The longitudinal axis preferably runs at an angle of about 90° to the second axis of rotation.

Further, it is possible that several uptake spaces are provided, and/or the second uptake space is divided into several individual spaces or chambers. One or more openings may be provided respectively between the individual chambers and/or uptake spaces and the first uptake space. Preferably, the size of the openings is respectively chosen as a function of the viscosity of the liquid. Preferably, the orientation of the openings is chosen in such a way that the centrifugal forces act on the openings.

A preferred embodiment of the mixing vessel according to (11) is shown in FIG. 4. The mixing vessel 48 shown in FIG. 4 can be provided within said uptake vessel 24. The mixing of the substances is then effected as described above by means of FIGS. 1 and 2.

The mixing vessel 48 has a first uptake space 50 and a second uptake space 52 for first and second substances, respectively. The first uptake space 50 is formed by a cylindrical body 54. Said body 54 is rotationally symmetrical to a longitudinal axis 56.

A conical body 58 forming the second uptake space 52 is arranged within the first uptake space 50. Said conical body is also rotationally symmetrical to the longitudinal axis 56.

The body 58 is inserted into an opening 60 of the cylindrical body 54 and secured at an edge 62 of the opening. The opening is sealed by a lid 64.

At a cone tip 66 of the conical portion 58 an opening 68 is provided. Thus, the opening 68 is provided in a separating wall 70 separating the first uptake space 50 from the second uptake space 52.

If the mixing vessel 48 is rotated around a first rotation axis 18 and a second rotation axis 28 as described above with reference to FIGS. 1 and 2, centrifugal forces act on the substance provided in the second chamber 52. This results in the substance being pressed or transferred through the opening 68 into the first uptake space. The truncated-cone-like design ensures substrate can be taken up laterally adjacent to the second uptake space within an annular area 72 if centrifugal forces are directed from the opening 68 towards the second uptake space 52. This prevents a transfer of larger substance amounts from the first uptake space 50 into the second uptake space 52. The conical design of the part 58 ensures the provision especially of an annular space 72. However, the second uptake space 52 might have a different shape, where it is preferred that the second uptake space 52 be surrounded by a space 72 in order to avoid substances to be pressed back from the first uptake space 50 into the second uptake space 52.

The second uptake space 52 may be separated into two or more chambers or spaces. Preferably, the second uptake space 52 is separated into two chambers. Here, it is preferred that each of the chambers has an opening arranged according to the opening 68 and having the same cross section. However, depending on the application, in particular on the viscosity of the liquid to be provided in the chambers or spaces, also other cross sections of the openings may be selected.

The mixing vessel 48 is preferably used if particle-containing formulations are to be redispersed (cf. example 9C). In this case the particle-containing formulation is provided in the first uptake space 50 and the redispersion medium is added to the second uptake space 52. Subsequently, the mixing vessel 48 is centrifuged as described above. Furthermore, it is preferably used if two phases are to be mixed with each other to obtain mixtures or lipid-containing nanoparticles (example 11). This use also enables a solvent in the lipid phase to be used (example 11C). Moreover, the mixing vessel 48 is preferably used in the application of the injection method and in the manufacture of lipoplexes. In other words: the mixing vessel according to embodiment (11) is preferably to be used for mixing processes.

Figure 8:
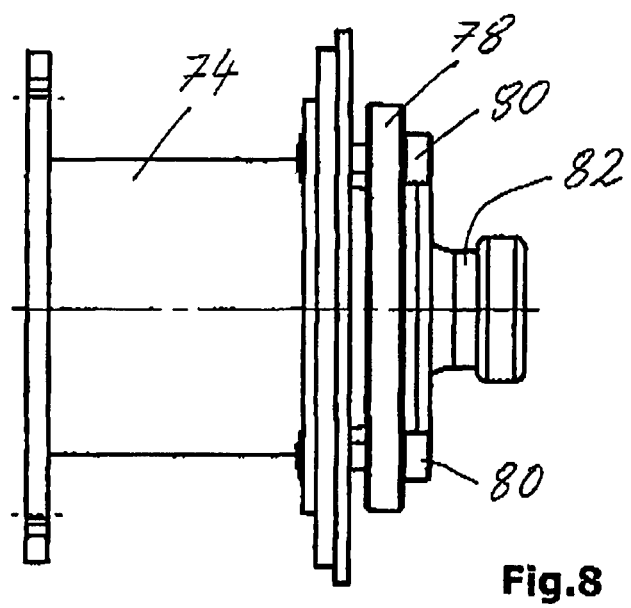
FIG. 8: mixing device of embodiment (13) for speed mixing an injection bottle
Figure 9:
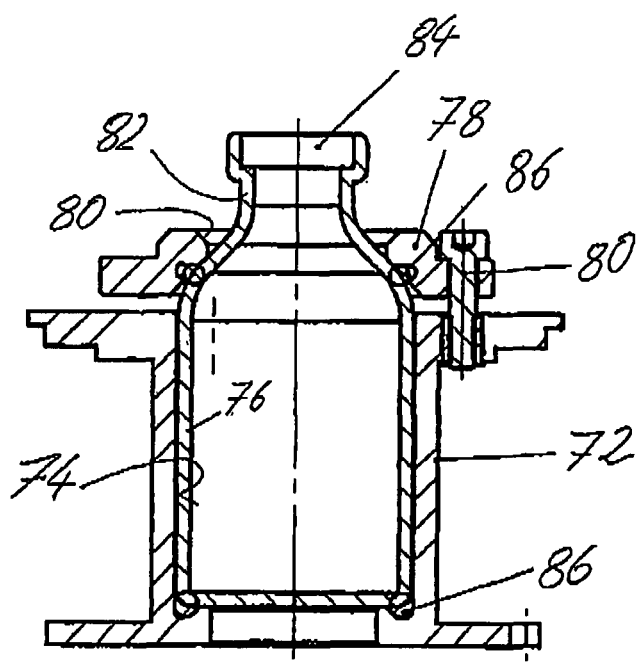
FIG. 9: schematic sectional view of the embodiment illustrated in FIG. 8

In another preferred embodiment of the invention an insert may be inserted into the uptake vessel 24. A first insert in particular serving for taking up an injection bottle is shown in FIGS. 8 and 9 (embodiment (13)). The insert 72 has an uptake space 74 which is cylindrical in the illustrated embodiment. The insert 72 may be secured in the uptake vessel by detent elements or other securing means. A mixing vessel 76 which may in particular be an injection bottle is insertable in the cylindrical uptake space. Here, the inner dimensions of the uptake space correspond to the outer dimensions of the injection bottle 76. Preferably, the outer wall of the mixing vessel 76 completely contacts the inner wall of the uptake space 74. However, the uptake space 74 may also have several webs the outer surface of the mixing vessel 76 rests against. In particular, three webs offset to each other by 120 degrees are provided.

A lid 78 is designed to hold the mixing device 76 within the uptake space 74. The lid 78 is secured to the insert 72 by screws 80 or other securing means. The lid 78 has an opening 80 through which a bottleneck 82 of the injection bottle 76 is introduced. Hence, a closure 84 of the injection bottle 76 is even accessible if the injection bottle 76 is introduced into the insert 72.

In order to prevent an injection bottle in particular made from glass to be damaged, annular dampening elements 86 are provided in the illustrated embodiment. In particular, the dampening elements are elastomeric rings. In this case, one dampening element is arranged in the bottom area of the uptake space 74, and one dampening element 86 is arranged in the lid 78. As can be learnt in particular from FIG. 9, the dampening elements prevent the injection bottle 76 to be damaged when closing the lid 78 using the screws 80. Thereto, the dampening elements 86 are arranged at the appropriate critical positions, in particular at the force transmission points in the lid. The dampening elements are in particular to fix the bottle in the insert. Thus, a counter-rotation of the bottle due to centrifugal forces is prevented.

Figure 10:
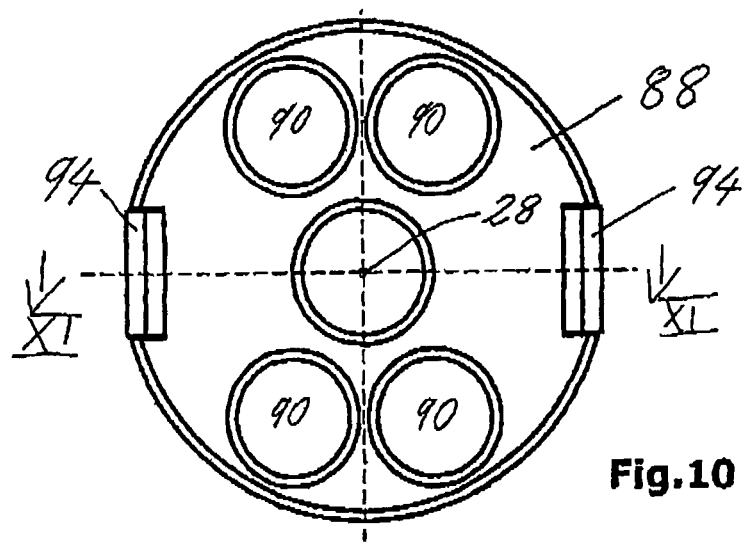
FIG. 10: mixing vessel for taking up Kryo-Vials or Eppendorf vessels which is also suited for low temperatures if suitable materials such as teflon, PE UHMW, aluminium are used
Figure 11:
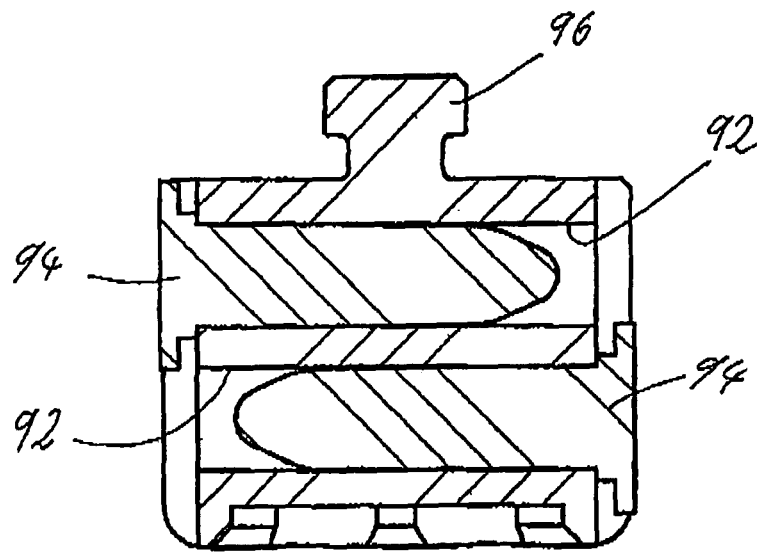
FIG. 11: sectional view along the line XI-XI in FIG. 10
Figure 12:
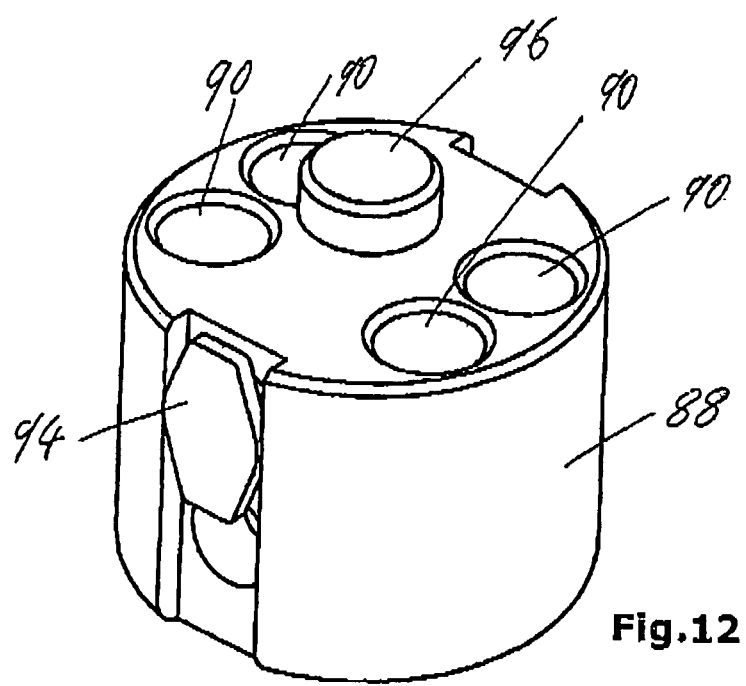
FIG. 12: schematic perspective view of the mixing vessel illustrated in FIGS. 10 and 11

An uptake vessel insert 88 (FIG. 10 to 12) may be provided for taking up mixing vessels 40 (FIG. 3), mixing vessels 48 (FIG. 4), Kryo-Vials or Eppendorf vessels and the like. In the illustrated embodiment, the uptake vessel 88 has six uptake spaces 90, 92. In the illustrated embodiment, the uptake spaces 90, 92 are arranged circular cylindrically. However, the uptake spaces may for example be formed by the provision of webs serving to fix the position of the mixing vessels. Here, all or at least some single webs may be elastic.

In the illustrated embodiment, the uptake spaces 90 are arranged in parallel to the second rotation axis 28. Thus, the longitudinal axes of the uptake spaces 90 runs parallel to the rotation axis 28 or perpendicular to the drawing plane of FIG. 10. The longitudinal axes of the uptake spaces 90 are spaced apart from the second rotation axis 28. The second uptake spaces 92 (FIG. 11) are arranged perpendicular to the second rotation axis.

In the illustrated embodiment, Eppendorf vessels 94 are inserted into the uptake spaces 92. In this case, the uptake spaces 92 are preferably provided as ports in the insert 88 enabling the Eppendorf vessels 94 to be inserted into the uptake spaces 92 from different sides.

The insert 88 has a handle element 96 to facilitate transporting. The handle element 96 is suited in particular also for introducing the insert into the uptake vessel 24 and for removing it therefrom.

Embodiment (12) comprising the mixing device according to embodiment (10) is suited for solving also shaking problems with the use of a DAC. For the mixing device according to (10) a DAC insert having vials introduced horizontally into the sample holder was developed (see FIGS. 3 and 10 to 12). Practically any laboratory shaking problem may be solved in an efficient, quiet and fast way.

The process developed here is much better than current processes (such as, e.g., Qbiogene's FastPrep®) since a 5 min break between separate shaking steps is not required and the equipment needed for shaking (DAC) may also be used for other tasks. Moreover, shaking in various vessels may be effected simply by exchanging the mixing vessel in the mixing device according to (10). When making the DAC insert from an insulating material such as styropor, deep frozen samples are kept cool for a longer time which is advantageous in particular in the breaking down of tissue since a gentle treatment of the material despite the required longer shaking of the sample is ensured. Using this technique, in particular also very small sample amounts may be broken down. Thereto, uptake vessels suited for low temperatures for sample vials are prepared (FIG. 10-12) which may securely be fastened in various types of so-called Kryo-Vials and Eppendorf® vessels. "Suited for low temperatures" means that said containers are made from a material being suited for uses at temperatures as low as −196° C. or in liquid nitrogen. The material used for making said uptake vessels is preferably teflon, PE, UHMW or aluminium. For uptake vessels not suited for low temperatures also other materials, in particular light-weight materials such as styropor and plastics may be used.

A DAC, in particular a DAC comprising the devices for the shaking process may also be used for mince solid matter, in particular for working up tissues and disrupting cells (example 17). "Disrupting" preferably means that solid matter exists as powders after the process has been carried out. The corresponding process according to embodiment (14) is performed with the addition of disintegration aids. Suitable disintegration aids are the dispersing aids described above, that is, pearls made from materials such as steel, agate, corundum and glass. Steel or glass beads are exceptionally preferred. The diameter thereof is preferably at least 3 mm, exceptionally preferred at least 5 mm. The preferred maximal diameter is 10 mm. Also mixtures of different disintegration aids (different sizes and/or different materials) may be used. If tissues are disrupted using the present process, they are of animal (also human) or plant origin. Cells to be disrupted may be either eukaryotic or prokaryotic.

The disruption of cells or tissues according to embodiment (14) may be effected not only at room temperature but also at low temperatures. Hereto, the sample is cooled or deep-frozen, e.g., by adding liquid nitrogen, and the disruption in the DAC is effected in a precooled uptake vessel suited for low temperatures described above (example 17, FIG. 10-12).

The process according to embodiment (14) may also be used to mince other samples than tissue or cells. Such other samples are all materials which may be crushed by triturating. Preferably, said materials are foodstuff, solid types of pharmaceutical preparations including tablets and granulates and crystalline organic or inorganic materials (cf. example 17). Preferably, this crushing serves in the sample preparation for analytics such as, e.g., in the preparation of moulded KBr pieces for infrared spectroscopy or the determination of the amount of active substances of a pharmaceutical.

In a way, the process according to embodiment (14) is a replacement of the classical mortar which is often difficult to handle and unsuited for small sample amounts. Preferably, it is suited for crushing small sample amounts (less than 1 g, in particular less than 300 mg) and for the handling of dangerous, toxic or radioactive substances.

Another advantage of the process (14) is that it may be performed in vessels having small volumes. Preferably, said volumes are maximally 10 ml, especially preferred up to maximally 2 ml. Even smaller volumes may be used. This enables to work with small biological samples and a time-saving crushing of a multitude of samples in parallel. Eppendorf® vessels and Kryo-Vials are preferred vessels.

The invention will be illustrated with reference to the following examples, which, however, do not limit the process of the invention.

EXAMPLES

In the following Examples, "speed mixing" means the use of a Speedmixer® (asymmetrical dual centrifuge) of the type DAC 150 FVZ from the company Hauschild GmbH &

Co KG, which has a counter-rotation ratio of about 4.2:1. "Eppi" means a 2 ml Eppendorf® vessel. Unless stated otherwise, percents are w/v. Unless stated otherwise, "size" of the lipid-based nanoparticles always means "mean size" in the following.

Example 1: Preparation of Vesicular Phospholipid Gels (VPG) and Liposomal Dispersions by DAC Technology; Comparison of the Formed Liposomes with Liposomes Prepared by Means of High-Pressure Homogenization 1.48 g of a mixture of EPC3 (hydrogenated egg lecithin, Lipoid) and cholesterol (55 mole %:45 mole %), which existed as a solid solution, was weighed into a 25 ml medicine bottle (outer diameter: 36 mm) and flange-sealed (vial 1). A second medicine bottle (vial 2) contained the same amount of lipid, but in this case 3.0 g of glass beads (diameter about 1 mm) was additionally added. Into both vials, 2.22 ml of mannitol solution (5%) was injected, and each of the vials was subjected to speed mixing at 3540 rpm at RT (room temperature) for 4.5 min. By adding 6.4 ml mannitol solution (5%) in 2 steps (step 1: 100 μl), the vesicular phospholipid gel (VPG) formed was redispersed (speed mixing for 1 min each), and the mean size of the liposomes was determined by photon correlation spectroscopy (PCS, Nicomp 370). The number of particles of >1 μm was determined by means of the light obscuration method (Nicomp, Accusizer). VPG prepared by high-pressure homogenization (same lipid mixture, same proportion of mannitol solution; 700 bar, 10 cycles) (vial 3) was also included in the determination. Also included in the examination of particles of >1 μm was a commercial lipid emulsion for parenteral nutrition (Nutriflex®, B. Braun).

TABLE 1

Comparison of the liposome size and the number of particles that are >1 μm after speed mixing without (vial 1) and with (vial 2) glass beads, after high-pressure homogenization (vial 3) and in a commercial lipid emulsion (Nutriflex®).

| Vial | Size of liposomes | Number of particles > 1 μm per ml (dilution: 1:20 million) |
|---|---|---|
| 1 | 171 nm | 173 |
| 2 | 36 nm | 97 |
| 3 | 36 nm | 209 |
| Nutriflex® | 190 nm | 58 |

Example 2: Preparation of Vesicular Phospholipid Gels (VPG) and Liposomal Dispersions by DAC Technology; Variation of the DAC Parameters (i) Mixing Speed, (ii) Vessel Diameter, (iii) Speed Mixing Time. (iv) Temperature Influence and (v) Addition of a Mixing Aid In the experiments described in the following, liposomes were prepared by means of DAC technology by analogy with Example 1 (same lipid mixture (mixture of EPC3 (hydrogenated egg lecithin, Lipoid) and cholesterol (55:45 mole %)), same aqueous medium (5% mannitol solution)). The speed of the Speedmixer®, the time of speed mixing, the diameter of the vessel employed for speed mixing and the temperature were varied. In addition, mixing was operated with and without the addition of a mixing aid, and for this purpose, glass beads were employed in these Examples.

The liposome gel formed during speed mixing was redispersed with three times the primarily employed aqueous volume, and the respectively formed liposomes were subsequently examined by PCS for their mean sizes.

TABLE 2

Effects of the variation of the speed mixing parameters

| Experiment No. | Mixing speed [rpm] | Temperature | Vessel type/ diameter [mm] | Time [min] | Glass beads [mg] | Scale [mg of lipid] | Particle size [nm] (bulk) |
|---|---|---|---|---|---|---|---|
| Influence of time | | | | | | | |
| 3a | 3540 | RT | Eppi/10 | 20 | 100 | 50 | 72.7 |
| 3b | 3540 | RT | Eppi/10 | 30 | 100 | 50 | 97.0 |
| 3c | 3540 | RT | Eppi/10 | 50 | 100 | 50 | 69.4 |
| 3d | 3540 | RT | Eppi/10 | 70 | 100 | 50 | 59.4 |
| 3e | 3540 | RT | Eppi/10 | 90 | 100 | 50 | 53.5 |
| Influence of temperature | | | | | | | |
| 11 | 3540 | 60° C. heating block silicone oil | Eppi/10 | 20 | 100 | 50 | 55.3 |
| 17b | 3540 | RT | Glass/10 | 5 | 100 | 50 | 79.7 |
| 18a | 3540 | 60° C. heating block silicone oil | Glass/10 | 5 | 100 | 50 | 40.3 |
| Influence of vessel and mixing aid (glass beads) | | | | | | | |
| X17b | 3540 | RT | Glass/10 | 5 | 100 | 50 | 79.7 |
| 17c | 3540 | RT | Glass/11 | 5 | 100 | 50 | 87 |
| 17d | 3540 | RT | Glass/15 | 5 | 100 | 50 | 53.6 |
| 17f | 3540 | RT | Glass/10 | 5 | — | 50 | 87.4 |
| 17g | 3540 | RT | Glass/11 | 5 | — | 50 | 271 |
| 17h | 3540 | RT | Glass/15 | 5 | — | 50 | 119.5 |
| Influence of mixing speed | | | | | | | |
| X17b | 3540 | RT | Glass/10 | 5 | 100 | 50 | 79.7 |
| 30a | 3000 | RT | Glass/10 | 5 | 100 | 50 | 285.1 |

TABLE 2-continued

Effects of the variation of the speed mixing parameters

| Experiment No. | Mixing speed [rpm] | Temperature | Vessel type/ diameter [mm] | Time [min] | Glass beads [mg] | Scale [mg of lipid] | Particle size [nm] (bulk) |
|---|---|---|---|---|---|---|---|
| 30b | 2000 | RT | Glass/10 | 5 | 100 | 50 | no liposome formation |

X: experiment is stated again for reasons of comparison

Example 3: Preparation of Vesicular Phospholipid Gels (VPG) and/or Liposomal Dispersions from Different Lipids/Mixtures of Lipids by DAC Technology In the experiments described in the following, liposomes were prepared by means of DAC technology by analogy with Examples 1 and 2. In this experiment, the lipid mixtures were varied. Table 3 shows the experiments in which lipid mixtures were employed that already existed as solid solutions or in which lipids of only one type were employed. Thus, the lipid mixtures were previously taken up in CHCl$_3$/MeOH 2:1, the solvent was removed by rotary evaporation, and the lipid film formed was dried under vacuum and scratched out of the flask, or the lipid mixture was supplied in an already molecular disperse form.

In the experiments set forth in Table 4, the lipids were employed as individual components. For comparison, values from Table 3 with lipid mixtures used as a solid solution were stated again (marked with "X" or "*").

The liposome gels formed upon speed mixing were redispersed with three times the primarily employed aqueous volume. The respectively formed liposomes were subsequently examined by PCS for their mean sizes.

TABLE 3

Experiments for the preparation of liposomes from lipid mixtures employed as solid solutions

| Experiment No. | Lipid composition | Scale [mg of lipid] | Vessel type/ diameter [mm] | Time [min] | Glass beads [mg] | Particle size [nm] (bulk) |
|---|---|---|---|---|---|---|
| Hydrogenated egg phosphotidylcholine/cholesterol (55/45 mol/mol): see Example 2 | | | | | | |
| Phosphatidylcholine from soybean (min. 80%, S80, Lipoid), 5% mannitol solution | | | | | | |
| 4a | E80 | 50 | Eppi | 20 | 100 | 52.7 |
| 4b | E80 | 50 | Eppi | 30 | 100 | 53.5 |
| 4c | E80 | 50 | Eppi | 40 | 100 | 52.4 |
| 8 | E80 | 50 | Eppi | 20 | 100 | 47.3 |
| Cationic lipids | | | | | | |
| 5a | DOTAP | 50 | Eppi | 20 | 100 | 57.7 |
| 31 | KL-1-14/Chol 1:0.55 | 50 | Eppi | 10 | 100 | 112.2 |
| Surfactant lipids (Aleofact, BI) | | | | | | |
| 21 | Surfactant lipids | ca. 50 | Original vial, glass diameter: 14 mm | 5 | — | 48.1 |
| Negatively charged lipid mixture | | | | | | |
| 32a | HEPC, Chol, DPPG | 50 | Eppi | 5 | 100 | 238.1 |
| Stealth liposomes | | | | | | |
| 29b | HePC/Chol/DSPE-PEG-2000 | 104 | Glass 11 mm | 25 | 1200 | 88.4 |

TABLE 4

Experiments relating to the preparation of liposomes from lipid mixtures employed as individual components in the experiments

| Experiment No. | Lipid composition | Scale [mg of lipid] | Vessel type/ diameter [mm] | Time [min] | Glass beads [mg] | Particle size [nm] (bulk) | Additional treatment |
|---|---|---|---|---|---|---|---|
| Hydrogenated egg phosphatidylcholine/cholesterol (55/45 mol/mol) | | | | | | | |
| 15a | EPC3/Chol | 800 | PE cup/14 | 20 | 1600 | 60.4 | |
| 15a | EPC3/Chol | 800 | PE cup/14 | 25 | 1600 | 54.8 | |

TABLE 4-continued

Experiments relating to the preparation of liposomes from lipid mixtures employed as individual components in the experiments

| Experiment No. | Lipid composition | Scale [mg of lipid] | Vessel type/ diameter [mm] | Time [min] | Glass beads [mg] | Particle size [nm] (bulk) | Additional treatment |
|---|---|---|---|---|---|---|---|
| 15a | EPC3/Chol | 800 | PE cup/14 | 30 | 1600 | 41.9 | |
| X2 Comparison | EPC3/Chol-ready mix from Lipoid | 1480 | Injection bottle/30 | 20 | 3000 | 36 | |
| 11 | EPC3/Chol | 50 | Eppi | 20 | 100 | no liposome formation | RT |
| 11a | EPC3/Chol | 50 | Eppi | 20 | 100 | 56.1 | heated at 60° C. |
| E80/Chol mixtures (in Eppi, in large PE cup with and without heating) | | | | | | | |
| 9 | E80/Chol | 50 | Eppi | 30 | 100 | 200.9 | |
| 13a | E80/Chol | 1200 | PE cup/14 | 1.5 | 2400 | 133.7 | |
| 13b | E80/Chol | 1200 | PE cup/14 | 10 | 2400 | 66.3 | |
| 13c | E80/Chol | 1200 | PE cup/14 | 15 | 2400 | 55.3 | |
| 13d | E80/Chol | 1200 | PE cup/14 | 20 | 2400 | 71.2 | |
| 13e | E80/Chol | 1200 | PE cup/14 | 25 | 2400 | 70.4 | |
| 14a | E80/Chol | 1200 | PE cup/14 | 1 | 2400 | 158.3 | heated at 60° C. |
| 14b | E80/Chol | 1200 | PE cup/14 | 5 | 2400 | 85.7 | heated at 60° C. |
| 14c | E80/Chol | 1200 | PE cup/14 | 10 | 2400 | 65.4 | heated at 60° C. |
| 14d | E80/Chol | 1200 | PE cup/14 | 15 | 2400 | 60.2 | heated at 60° C. |
| 14e | E80/Chol | 1200 | PE cup/14 | 20 | 2400 | 54 | heated at 60° C. |
| Cationic lipid KL-1-14/chol (variation: mixing time and temperature) | | | | | | | |
| 26a | KL-1-14/Chol | 50 | Eppi | 20 | 100 | 371.2 | |
| 26b | KL-1-14/Chol | 50 | Eppi | 30 | 100 | 298.9 | |
| 26c | KL-1-14/Chol | 50 | Eppi | 40 | 100 | 299.9 | |
| 26d | KL-1-14/Chol | 50 | Eppi | 50 | 100 | 197.7 | heated at 60° C. |
| X 31 | KL-1-14/Chol* 1:0.55 | 50 | Eppi | 10 | 100 | 112.2 | |
| Stealth liposomes | | | | | | | |
| 29a | HePC/Chol/DSPE-PEG-2000 | 114 | Glass/10 | 25 | 1500 | 70.3 | |
| X 29b | HePC/Chol/DSPE-PEG-2000* | 114 | Glass/10 | 25 | 1500 | 88.4 | |

X: Comparative experiments with lipid mixtures employed as solid solutions;
*solid solution of lipid mixtures Example 4: Preparation of Surfactant-Like Liposomes that can be Introduced into the Lung for Therapeutic Purposes A) Surfactant-Like Liposomes without Specific Active Ingredients.

(composition according to Wissel et al., Am J Physiol 271: L432-40 (1996); or Müller, B. et al., Thorax 58: 127-134 (2003); or al-Mehdi, A. B. et al., BBA 1167: 56-62 (1993)). The liposomes were prepared by analogy with the procedure described above by speed mixing. All operations were performed in a laminar flow hood. The lipid composition was DPPC (Sigma P5911)/PG (Sigma P05141)/EPC (Lipoid)/cholesterol at a weight ratio of 5.5/1/2.5/1. The lipids were weighed, taken up in chloroform/MeOH 2:1, the solvent was removed by rotary evaporation, and the lipid film formed was dried. 50 mg of this lipid mixture was then weighed into an autoclaved speed mixing vessel (glass vial, 10 mm), 100 mg of autoclaved glass beads was added, and a volume of 75 µl of sterile-filtered PBS (25 mM $NaH_2PO_4$, 125 mM NaCl, pH 6.9) was added and subjected to speed mixing in a closed vessel for 10 minutes. It was subsequently redispersed with 250 µl of PBS. Liposomes having a size of 74.6 nm were obtained.

B) Surfactant-Like Liposomes with Fluorescence (NBD; Rhodamine) and Radioactive ($^3$H) Label.

For this experiment, the following lipids were weighed into a sterile glass vessel or added as a solution in $CHCl_3$/MeOH 2:1: DPPC, 81.2 mg (Sigma P5911)/PG, 17.1 mg (Sigma P05141)/EPC, 42.7 mg (Lipoid)Cholesterol, 17.1 mg/rhodamine-PE, 1.7 mg/NBD-PC 7.7 mg/$^3$H-DPPC (1.46 nCi/µg DPPC). The mixture was dissolved completely with $CHCl_3$/MeOH 2:1 in a speed mixing vessel (glass 15 mm), and the solvent was carefully evaporated to dryness in a nitrogen flow. 250 µl of sterile PBS buffer and 350 mg of sterile glass beads (diameter 1 mm) were added, and the mixture was subjected to speed mixing in a closed vessel for 1 minute. The vesicles of the finished liposomal dispersion had a mean size of 83.5 nm.

B) Surfactant-Like Liposomes with a Lipidic sPLA2 Inhibitor as an Anti-Inflammatory Drug.

DPPC, PG, EPC, cholesterol and the sPLA2 inhibitor 2-(R)-1-O-phosphocholine-2-N-laurinoyloctadecane in the weight ratios 50/10/25/10/5 were commonly weighed and dissolved in CHCl$_3$/methanol 2:1. The solvent was removed by rotary evaporation, and the lipid film formed was freed from solvent residues under vacuum, and the lipid mixture was scratched out of the flask. A quantity of 100 mg of lipid mixture was weighed into a sterile glass vessel, 200 mg of sterile glass beads (diameter 1 mm) was added, and 150 µl of PBS buffer (10 mM NaH$_2$PO$_4$, 149 mM NaCl, pH 6,9) was added. The mixture was subjected to speed mixing for 15 minutes, and then the gel formed was redispersed with 9.8 ml PBS. The vesicles of the finished dispersion had a mean size of 74.3 nm.

Example 5: Direct Preparation of Vesicular Phospholipid Gels (VPG) Loaded with Substances and Liposomal Dispersions by DAC Technology A) Direct Inclusion of Albumin in Liposomes.

Into six sterile glass vials (diameter 10 mm), 100 mg each of glass beads (diameter 1 mm) and 50 mg each of the mixture of hydrogenated egg phosphatidylcholine and cholesterol (55/45 mole %) existing as a solid solution was weighed. Into three of the vials, 75 µl each of an albumin solution was pipetted in concentrations of 1, 2 and 3 mg/ml. Into the fourth to sixth vials, 75 µl each of NaCl solution having a concentration of 0.9% was added. The closed vials were subjected to speed mixing at 3540 rpm for 10 minutes each. The three liposome gels loaded with albumin were redispersed with 250 µl each of NaCl solution. In contrast, the liposome gels prepared with saline only (vials 4-6) were redispersed with 175 µl of NaCl solution plus 75 µl of albumin solution (1, 2, 3 mg/ml). Subsequently, the thus formed liposomal dispersions were pipetted into suitable centrifuge tubes and centrifuged at 350,000 g, whereupon the liposomes sedimented. In the supernatant, the albumin concentration was subsequently determined by means of a BCA test (Interchim/Uptima, No. UP95424), and the inclusion efficiency was calculated. Result of inclusion efficiency for albumin in liposomes by speed mixing:
1 mg/ml albumin: 60.9%; 2 mg/ml albumin: 70.9%; 3 mg/ml albumin: 71.8%

B) Direct Inclusion of Trypan Blue in Liposomes as an Example of Low-Molecular Weight Drugs.

Into two glass vials (diameter 10 mm), 100 mg each of glass beads (diameter 1 mm) and 50 mg each of the mixture of hydrogenated egg phosphatidylcholine and cholesterol (55/45 mole %) existing as a solid solution was weighed. Into one vial, 75 µl of a trypan blue solution (1000 µl of commercially available trypan blue solution (0.4%) plus 30 ml of 25% ammonia solution) was pipetted. Into the second vial, 75 µl of 0.9% NaCl solution was added. The closed vials were subjected to speed mixing at 3540 rpm for 10 minutes each. The liposome gel loaded with trypan blue solution was redispersed with 250 µl of NaCl solution. The liposome gel prepared with saline only was redispersed with 175 µl of NaCl solution plus 75 µl of trypan blue solution. Subsequently, both liposomal dispersions were pipetted into suitable centrifuge tubes and centrifuged at 350,000 g, whereupon the liposomes sedimented. In the supernatant, the trypan blue concentration was subsequently determined by absorption spectroscopy, and the inclusion efficiency was calculated. Result of inclusion efficiency for trypan blue in liposomes by speed mixing: 51%

C) Direct Inclusion of Fluorescence-Labeled RNA in Neutral Liposomes as Well as in Liposomes Having a Negative Surface Charge.

i) Neutral Liposomes:

Into two glass vials (diameter 10 mm), 100 mg each of glass beads (diameter 1 mm) and 50 mg each of the mixture of hydrogenated egg phosphatidylcholine and cholesterol (55/45 mole %) existing as a solid solution was weighed. Into one vial, 75 µl of a 1 µM RNA-Cy3 solution (RNA: 27mer; 5'-GGA GCU CGC U TC GGC GAG GUC GUG CCA-3'; T=thymidine-C6-amino-NHS-Cy3; Cy3: fluorescence dye; Qiagen) was pipetted. Into the second vial, 75 µl of NaCl solution was added. The closed vials were subjected to speed mixing at 3540 rpm for 10 minutes each. The liposome gel loaded with RNA-Cy3 solution was redispersed with 250 µl of NaCl solution. The liposome gel prepared with saline only was redispersed with 175 µl of NaCl solution plus 75 µl of RNA solution. Subsequently, both liposomal dispersions were pipetted into suitable centrifuge tubes and centrifuged at 100,000 rpm, whereupon the liposomes sedimented. In the supernatant, the relative concentrations of fluorescence-labeled RNA were subsequently determined by fluorescence spectroscopy (em: 565, ex; 515 nm), and the inclusion efficiency for RNA-Cy3 was calculated by dividing the values by one another (60.1%). The mean size of the redispersed vesicles was determined by means of PCS to be 127.8 nm.

ii) Negatively Charged Liposomes:

Into two glass vials (diameter 10 mm), 100 mg each of glass beads (diameter 1 mm) and 50 mg each of the mixture of hydrogenated egg phosphatidylcholine and cholesterol and dipalmitoylphos-phatidylglycerol (DPPG) (46/33/20 mole %) existing as a solid solution was weighed. Into one vial, 75 µl of a 1 µM RNA-Cy3 solution (RNA: 27mer; 5'-GGA GCU CGC U TC GGC GAG GUC GUG CCA-3'; T=thymidine-C6-amino-NHS-Cy3; Cy3: fluorescence dye; Qiagen) was pipetted. Into the second vial, 75 µl of NaCl solution was added. The closed vials were subjected to speed mixing at 3540 rpm for 10 minutes each. The liposome gel loaded with RNA-Cy3 solution was redispersed with 250 µl of NaCl solution. The liposome gel prepared with saline only was redispersed with 175 µl of NaCl solution plus 75 µl of RNA solution. Subsequently, both liposomal dispersions were pipetted into suitable centrifuge tubes and centrifuged at 100,000 rpm, whereupon the liposomes sedimented. In the supernatant, the relative concentrations of fluorescence-labeled RNA were subsequently determined by fluorescence spectroscopy (em: 565, ex: 515 nm), and the inclusion efficiency for RNA-Cy3 was calculated by dividing the values by one another (82.9%). The mean size of the redispersed vesicles was determined by means of PCS to be 238.1 nm.

D) Direct Inclusion of Gemcitabine in Vesicular Phospholipid Gels by Speed Mixing.

Into a 25 ml injection bottle (outer diameter: 36 mm), 1.48 g of the mixture of hydrogenated egg phosphatidylcholine and cholesterol (55/45 mole %) existing as a solid solution as well as 3 g of glass beads (diameter 1 mm) was weighed under sterile conditions. The bottle was flange-sealed. Through the septum, 500 µl of a Gemzar® solution (containing 38.02 mg of gemcitabine/ml; Gemzar® is the name of the gemcitabine-containing medicament of the company Lilly, one injection bottle contains 200 mg of gemcitabine (lyophilized) and is reconstituted with 5 ml of 0.9% NaCl) as well as 2.22 g of 5% mannitol solution was added. The mixture was subjected to speed mixing at 3540 rpm for 20 minutes to form gemcitabine-containing VPG.

The inclusion efficiency for gemcitabine was 80.7% (method: Moog et al., Cancer Chem Pharmacol 49: 356

(2002)), the Lyso-PC content was less than 0.5% LysoPC/total lipid (by means of HPTLC), the mean size of the vesicles was 38.7 nm (PCS).

Thus, it could be shown that gemcitabine can be included in VPG by speed mixing, and that the product is comparable with gemcitabine-containing VPG in which the empty VPG was prepared by high-pressure homogenization, and gemcitabine was incorporated later by passive loading (EP 1 087 752) (inclusion efficiency for passive loading: 43-47%). However, the method performed here is evidently milder, which is shown by the low Lyso-PC content of the formulation (content for high-pressure homogenization and subsequent passive loading: 3-50%).

E) Direct Inclusion of Bendamustine in Vesicular Phospholipid Gels by Speed Mixing.

Into a 25 ml injection bottle (outer diameter: 36 mm), 1.0 g of the mixture of hydrogenated egg phosphatidylcholine and cholesterol (55/45 mole %) existing as a solid solution as well as 1.0 g of glass beads (diameter 1 mm) was weighed under sterile conditions. The bottle was flange-sealed. Through the septum, 1.5 ml of a Bendamustin® hydrochloride solution (containing 9.09 mg of bendamustine/ml; the solution was prepared by reconstitution from Bendamustin of Ribosepharm; thus, 0.9% NaCl solution was injected into the medicine bottle with the lyophilized medicament) was added. The mixture was subjected to speed mixing at 3540 rpm for 30 minutes to form a VPG containing bendamustine hydrochloride. Samples of the VPGs containing bendamustine were taken, and the inclusion efficiency for bendamustine was determined to be 40.6±3.08% (SD) (separation of the free bendamustine: by ion exchanger, Moog et al., Cancer Chem Pharmacol 49: 356 (2002), bendamustine analytics: Maas, B. et al., Pharmazie 49: 775-777 (1994)). The mean size of the vesicles was determined by PCS to be 62.5±3.5 nm (SD) (n: 8).

F) Direct Preparation of a Vesicular Phospholipid Gel Using a Silicon Dioxide Dispersion 10% Phospholipid in Silicon Dioxide Dispersion:

2.25 g of a silica gel with 2.8 g of silica anhydride/100 ml of water was admixed with 250 mg of S80. The mixture was subjected to speed mixing at 3540 rpm in a PE cup (diameter about 34 mm) for 20 minutes to form a creamy formulation which can be easily redispersed in water. The particle size was determined by PCS and was around 31.5 nm.

15% Phospholipid in Silicon Dioxide Dispersion:

2.15 g of a silica gel with 2.8 g of silica anhydride/100 ml of water was admixed with 0.38 g of S80. The mixture was subjected to speed mixing at 3540 rpm in a PE cup (diameter about 34 mm) for 20 minutes to form a creamy formulation which can be easily redispersed in water. The particle size was determined by PCS and was around 31.3 nm.

30% Phospholipid in Silicon Dioxide Dispersion:

1.76 g of a silica gel with 2.8 g of silica anhydride/100 ml of water was admixed with 710 mg of S80. The mixture was subjected to speed mixing at 3540 rpm in a PE cup (diameter about 34 mm) for 20 minutes to form a creamy formulation which can be easily redispersed in water. The particle size was determined by PCS and was around 64.5 nm.

40% Phospholipid in Silicon Dioxide Dispersion:

1.49 g of a silica gel with 2.8 g of silica anhydride/100 ml of water was admixed with 1004 mg of S80. The mixture was subjected to speed mixing at 3540 rpm in a PE cup (diameter about 34 mm) for 20 minutes to form a creamy formulation which can be easily redispersed in water. The particle size was determined by PCS and was around 85.2 nm.

Example 6: Incorporation of a Water-Insoluble Drug in Prefabricated VPGs to Solid Lipid Nanoparticles (SLN), Screening for a Suitable Drug-to-Lipid Ratio A) Incorporation in Liposomes.

It should be examined whether and in what proportions the water-insoluble drug PQ013 (PQ: Prokinase GmbH, Freiburg, Germany; MG: 399.4 g/mol) can be incorporated into prefabricated liposomes. Thus, liposome gels were prepared from E80 (phosphatidylcholine preparation from egg, Lipoid, Ludwigshafen, Germany) by speed mixing (500 mg of E80, PE cup with diameter 34 mm, 750 µl 0.9% NaCl, speed mixing at 3540 rpm for 10 min). Increasing amounts of PQ013 were weighed into glass vials (diameter 10 mm) or, for very small amounts, dissolved in dioxan and pipetted in. In the latter case, the solvent was subsequently removed under vacuum. 125 mg each of the E80 gel (contains 50 mg of S80, about 68 µmol) was added to the vials, and speed mixing was performed at 3540 rpm at 30 minutes. Subsequently, 1 ml each of PBS was added and redispersed for 2 minutes. 100 µl of the respective liposomal formulations was pipetted into a 24-well microtitration plate, briefly subjected to initial centrifugation and then examined microscopically for the presence of PQ013 crystals. It was found that no more crystals appeared for a molar ratio of PQ013 to lipid of lower than 1:40, i.e., PQ013 is completely soluble in a more than 40 fold molar excess of phospholipid (E80).

| | Mixture | | | | | | | |
|---|---|---|---|---|---|---|---|---|
| | 1 | 2 | 3 | 4 | 5 | 6 | 7 | 8 |
| PQ013 [µmol] | 68 | 6.8 | 3.4 | 1.7 | 1.13 | 0.68 | 0.14 | 0.068 |
| PQ013 [mg] | 27.2 | 2.72 | 1.36 | 0.68 | 0.45 | 0.27 | 0.06 | 0.03 |
| Ratio (molar) | 1:1 | 1:10 | 1:20 | 1:40 | 1:60 | 1:100 | 1:500 | 1:1000 |
| Crystals | yes | yes | yes | no | no | no | no | no |

An analogous experiment was performed with liposomes made of pure hydrogenated phosphatidylcholine from egg (EPC, Lipoid). In this case, PQ013 could also be dissolved in the liposomes from a molar ratio of 30:1 of lipid to drug.

B) Incorporation into SLN. It should be examined whether and in what proportions the water-insoluble drug PQ013 (PQ: Prokinase GmbH, Freiburg, Germany; MW: 399.4 g/mol) can be incorporated into prefabricated SLNs. Thus, SLNs according to Example 15 were prepared by speed mixing, but they were not redispersed/diluted, but further employed as a viscous mass. Increasing amounts of PQ013 were weighed into glass vials (diameter 10 mm) or, for very small amounts, dissolved in dioxan and pipetted in. In the latter case, the solvent was subsequently removed under vacuum. 125 mg each of the SLN gel (contains 33.8% trimyristine, i.e., 42.3 mg; 58.4 µmol) was added to the vials, the vials were heated at 80° C., followed by speed mixing at 3540 rpm at 30 minutes (6×5 minutes with intermediate heating). Subsequently, 1 ml each of PBS was added and redispersed for 2 minutes. The samples were left in the refrigerator at 4-8° C. for 3 hours in order that the SLNs become solid. 100 µl each of the respective dispersions was pipetted into a 24-well microtitration plate, briefly subjected to initial centrifugation and then examined microscopically for the presence of PQ013 crystals. It was found that no more crystals appeared for a weight ratio of PQ013 to SLN of smaller than 1:500. PQ013 is completely soluble in a 500 fold molar excess of trimyristine (SLN).

| | Mixture | | | | | | | |
|---|---|---|---|---|---|---|---|---|
| | 1 | 2 | 3 | 4 | 5 | 6 | 7 | 8 |
| PQ013 [µmol] | 58.4 | 5.8 | 2.92 | 1.46 | 0.98 | 0.58 | 0.12 | 0.058 |
| PQ013 [mg] | 23.4 | 2.32 | 1.17 | 0.58 | 0.39 | 0.23 | 0.05 | 0.02 |
| Ratio (molar) | 1:1 | 1:10 | 1:20 | 1:40 | 1:60 | 1:100 | 1:500 | 1:1000 |
| Crystals | yes | yes | yes | yes | yes | yes | no | no |

Example 7: Preparation of Immunoliposomes by Speed Mixing

This Example is to demonstrate the simple preparation of immunoliposomes by speed mixing, which is mild towards the coupling lipid.

A) Immunoliposomes with IgG.

37.7 mg of hydrogenated EPC, 10.8 mg of cholesterol, 6.6 mg of DSPE-PEG-2000 and 0.44 mg of DSPE-PEG-2000-maleimide was weighed into a glass vial (diameter 10 mm) together with 100 mg of glass beads (diameter 1 mm). The lipids were dissolved with 150 µl of $CHCl_3$/MeOH 2:1, and then the solvent was removed again by a nitrogen flow to leave a lipid film. Solvent residues were removed over night under vacuum.

80 µl of HEPES buffer (20 mM HEPES, 130 mM NaCl, pH: 6.8) was added, the closed vial was incubated at 37° C. for 5 minutes, followed by speed mixing at 3540 rpm for 10 minutes.

Non-specific IgG was thiolated with 2-iminothiolane according to Huwyler, J. et al., Proc. Natl. Acad. Sci. USA 93: 14164-14169 (1996). The thiolated antibody was subsequently freed from excess iminothiolane by dialysis in borate buffer, pH 8.0, and concentrated to a volume of about 500 µl. The IgG solution was added to the liposome gel, and the mixture was subjected to speed mixing for redispersing for 30 seconds, and the mixture was incubated at RT for two hours. Subsequently, the liposomes could be further diluted and separated from unbound antibody by chromatography on Sephadex® G50.

B) Immunoliposomes with an LDL-Binding Peptide.

A lipid film was prepared at first. Thus, 120 mg of EPC3/cholesterol (55:45 mole:mole), 16.4 mg of DSPE-MPEG (2000), 8 mg of DSPE-PEG-maleimide and 0.500 µl of a 1 mg/ml solution of the fluorescent dye lissamine rhodamine-PE in chloroform/MeOH 2:1 (i.e., 0.5 mg of lissamine) was added to a 25 ml flask and dissolved with about 5 ml of $CHCl_3$/MeOH 2:1. The solvent was removed by means of a rotary evaporator to leave a reddish-glassy lipid film. It was dried over night under vacuum, scratched from the flask and stored under dry conditions.

20 mg of this lipid mixture was added to a 10 ml glass vial for flange-sealing (outer diameter 20 mm) in which 100 my of glass pearls (diameter 1 mm) were provided. Through the septum, 40 µl of a 0.35 M fosphenytoin solution (in 150 mM borate buffer plus 100 mM EDTA, pH 8) was added, and the mixture was subjected to speed mixing for 30 s at first and then, after another 5 min, for 5 min at 3540 rpm. Subsequently, 50 µl of a peptide solution containing 30 nmol of a 26 AA peptide from the binding region of human ApoA4 with a mercaptopropionic acid at the N terminus (for binding to the maleimide group on the liposomes) as well as 100 µl of 150 mM borate buffer (plus 100 mM EDTA) was added to the viscous liposome dispersion and subjected to speed mixing for 2 min. It was incubated over night at RT, the liposome dispersion was subsequently diluted with 2 ml of PBS (1 mM, pH 6, plus 150 mM NaCl), and the unbound peptide and the non-included fosphenytoin were separated off by gel filtration on Sephadex® G-59 Fine.

Example 8: Uniform and Quick Incorporation of Drugs Among the Vesicles of Prefabricated VPGs by Speed Mixing In these experiments, it was to be shown that drugs/dyes can be incorporated quickly into prefabricated VPGs (VPG preparation, for example, by high-pressure homogenization). This aims at a uniform distribution of the drug/dye among the vesicles, which is an important precondition of passive loading. In the following Examples, the incorporation of trypan blue as a model drug as well as of gemcitabine as a relevant drug among the vesicles for prefabricated VPGs by speed mixing.

A) Quick Incorruption of a Model Drug (Trypan Blue).

Into a 25 ml injection bottle of clear glass, 1 g of VPG (660 mM lipid, mixture of hydrogenated egg phosphatidylcholine and cholesterol (55/45 mole %), existing as a solid solution) was charged, and the bottle was centrifuged briefly, so that a uniformly thick layer of VPG formed at the bottom of the vessel. To this layer, 135 µl of a 0.04% trypan blue solution was added, and the vessel was subjected to speed mixing at 3540 rpm for 1 minute. By an exact visual Inspection, it was established that the dye was uniformly incorporated into the VPG.

B) Quick Incorporation of Gemcitabine.

Into a 25 ml injection bottle, 3.7 g of VPG (660 mM lipid, mixture of hydrogenated egg phosphatidylcholine and cholesterol (55/45 mole %), existing as a solid solution) was charged, and the bottle was centrifuged briefly, so that a uniformly thick layer of VPG formed at the bottom of the vessel. To this layer, 500 µl of a Gemzar® solution was added (contains 38.02 mg of gemcitabine/ml; Gemzar® is the name of the gemcitabine-containing medicament of the company Lilly, one injection bottle contains 200 mg of gemcitabine (lyophilized) and is reconstituted with 5.0 ml of 0.9% NaCl). The mixture was subjected to speed mixing at 3540 rpm for 0.5 minute.

Subsequently, the VPG-gemcitabine mixture as well as a comparative sample in which gemcitabine was incorporated into the VPG by two shaking steps for 10 and 5 minutes, respectively, with an incubation break for 1 hour between, incubated at 60° C. for 2 hours for passive loading, the VPG was subsequently redispersed, and the inclusion efficiency for gemcitabine was determined.

Inclusion efficiency when the gemcitabine was incorporated by speed mixing: 44%.

Inclusion efficiency when the gemcitabine was incorporated by shaking: 47%.

Example 9: Quick and Safe Redispersing of Empty and Drug-Containing Viscous Particle-Containing Drug Formulations by Speed Mixing/Mixing by Means of DAC A) Redispersing a VPG by Speed Mixing and Addition of the Dilution Medium (Redispersing Medium) in Several Steps (i) 3.7 g of a VPG (prepared by high-pressure homogenization (700 bar, 10 cycles) of a mixture of hydrogenated egg phosphatidylcholine and cholesterol (55/45 mole %) existing as a solid solution) was weighed into a 25 ml injection bottle and centrifuged briefly. Subsequently, 500 µl of NaCl solution was added at first for redispersing, and speed mixing was performed for 1 minute. Subsequently, 6.4 ml of NaCl solution was added, followed by speed mixing again for 1 minute. The dispersion formed was homogeneous and free from large particles, and the determination of vesicle size by PCS yielded 28.1 nm.

(ii) To 4.2 g of a gemcitabine-containing VPG (prepared by high-pressure homogenization (700 bar, 10 cycles) of a mixture of hydrogenated egg phosphatidylcholine and cholesterol (55/45 mole %) existing as a solid solution, followed by passive loading with gemcytabine hydrochloride) in a 25 ml injection bottle, 500 µl of NaCl solution was added at first, followed by speed mixing for 1 minute. Subsequently, 5.9 ml of NaCl solution was added, followed by speed mixing again for 1 minute. The dispersion formed was homogeneous and free from large particles, and the determination of vesicle size by PCS yielded 37.8 nm.

B) Redispersing of a VPG by One Addition of the Diluting Medium.

1.0 g of a VPG (prepared by high pressure homogenization of a mixture of hydrogenated egg phosphatidylcholine and cholesterol (55/45 mole %) existing as a solid solution) was weighed into a 25 ml injection bottle, 2 g of glass beads (diameter about 5 mm) was added, and the mixture was centrifuged briefly. Subsequently, 2.0 ml of NaCl solution was added for redispersing, followed by speed mixing for 2 minutes. The dispersion formed was homogeneous and free from large particles, and the determination of vesicle size by PCS yielded 35.9 nm.

C) Redispersing by Adding the Dilution Medium by Means of an Applicator.

Here, the redispersing medium was added by an applicator (FIG. 4): Into a glass vial (inner diameter about 13 mm), a 0.5 ml Eppendorf vessel that had a small bore at the bottom end was placed. The bore was so small that no aqueous solution could drop through. Into the Eppendorf vessel, 250 µl of the 5% mannitol solution was added (redispersing medium), and 125 mg of a VPG (prepared by high pressure homogenization of a mixture of hydrogenated egg phosphatidylcholine and cholesterol (55/45 mole %) existing as a solid solution) was added to the glass vial. The glass vial was closed, whereby the Eppendorf vessel was simultaneously fixed. The construct was subjected to speed mixing for 30 seconds. The formed dispersion was homogeneous and free of large particles, and the determination of vesicle size by PCS yielded 36.8 nm.

D) Redispersing of a Liposome-Containing Cream.

200 mg of "Aloe Vera Liposomen Gel" of the company Anton Hübner was weighed into a PE cup (inner diameter about 14 mm) and admixed with 2 ml of water. The mixture was subjected to speed mixing for 2 minutes, and the dispersion formed was homogeneous and free from large particles.

E) Sample Preparation in the Size Determination in a Silicon Dioxide Dispersion.

1 g of a SiO$_2$ dispersion (2.8 g of SiO$_2$/100 ml) was admixed with 1 g of glass beads (diameter 1 mm) as well as 9 ml of water and subjected to speed mixing in a PE cup (inner diameter about 34 mm) for 10 minutes. Subsequently, a size determination could be performed with PCS and yielded a readily measurable particle size of 55 nm.

Example 10: Reproducible Preparation of a Surfactant Dispersion with Small Vesicles from Lyophilized Surfactant by Speed Mixing Two bottles of Alveofact dry ampoule were used for the experiment (inner diameter about 13 mm). One bottle was rehydrated with the prescribed amount of NaCl solution according to the manufacturer's instructions and extruded (see Alveofact dry ampoule technical information). A second bottle was charged with the same amount of NaCl solution, but then treated in a Speedmixer® at 3540 rpm for 5 minutes. The mean sizes of the vesicles formed were determined by PCS and compared. In addition, the dispersions were stored at 4° C. for 9 days and then measured again.

Vial I (Preparation According to the Manufacturer's Instructions):
  Heavy foaming, exact measuring of the suspension not possible.
  Particles: 67.5 nm (the PCS measurement yields a very broad distribution ranging up to 5 µm). Isolated small flakes still to be seen.
  After 9 days at 4-8° C.: A precipitate has formed. Particle sizes were determined to be 132.9 nm, which means a clear particle growth. Also, the enormous broadness of the distribution (quite many particles have particle diameters of above 5 µm) suggests the presence of very large particles.
Vial II (Preparation by Speed Mixing):
  No foam, clean measuring possible.
  Particles: 48.1 nm (clearly narrower particle distribution ranging up to 1 µm in PCS).
  The dispersion seems to shrink from contact with the glass wall, formation of large vacuoles upon shaking: This means a much reduced surface tension of the dispersion, corresponding to that of the pulmonary surfactant.
  After 9 days at 4-8° C.: Particle size: 48.8 nm. Thus, the primarily prepared dispersion has not changed. In contrast to vial I, no precipitate was observed.

Example 11: Preparation of Liposomes from Solutions of Lipids in Organic Solvents and an Aqueous Phase by Speed Mixing In this Example, liposomes were combined by a combination of the injection method with the liposome preparation method by speed mixing. For this purpose, a glass vial (inner diameter about 13 mm) was filled with 100 mg of glass beads (diameter about 1 mm). Into the neck of the vial, a 0.5 ml Eppendorf vessel having a small bore at the lower end was inserted. The bore was so small that neither water nor ethanol dropped through.

A) Charging the Lipids in Organic Solvents, Addition of the Aqueous Phase Through an Applicator.

Into the glass vial, a solution of 80 mg of S80 in 100 µl of ethanol was charged. The Eppendorf vessel was engaged over the vial and filled with 400 µl of NaCl solution. The construct was screwed down, which also stabilized the engaged Eppendorf vessel. Subsequently, speed mixing was performed at 3540 rpm for 5 minutes to form a slightly turbid and highly viscous gel. Another 500 µl of NaCl solution was added to the upper Eppendorf vessel, and the construct was subjected to speed mixing for another 5 minutes. A liposomal formulation was produced, and the mean size of the liposomes was determined to be 122.7 nm by PCS.

B) Charging the Lipids in Organic Solvents, Stepwise Addition of the Aqueous Phase.

Experiment I was repeated in such terms that the first 400 µl of NaCl solution was added in 100 µl portions to the ethanolic solution of S80, and the mixture was subjected to speed mixing for 2 minutes each. Subsequently, as in Experiment I, the remaining 500 µl of NaCl solution was added at once, and speed mixing was again performed for 5 minutes. The mean size of the liposomes formed was determined to be 116.1 nm.

C) Charging of the Aqueous Phase, Addition of the Lipids in Organic Solvents with an Applicator.

Into the glass vial, 900 µl of NaCl solution was charged, and a solution of 80 mg of S80 in 100 µl of ethanol was added to the engaged Eppendorf vessel. The construct was subjected to speed mixing for 10 minutes. The liposomes formed were determined to be 83.9 nm by means of PCS.

Example 12: Reliable and Quick Incorporation of Liposomes into Ointments, Creams and Gels and their Bases Into a commercially available cream (vanishing cream with evening primrose oil from the company Anton Hübner), dispersions containing silicon dioxide particles were incorporated. Use was made of dispersions containing about 2 g. of silicon dioxide/100 ml as well as 10, 15, 30 and 40% of the phospholipid S 80 (for its preparation, see Example 5F). Thus, 1.2 to 2.3 g of the cream was weighed into a PE cup (inner diameter about 34 mm), and various proportions of 10-50% by weight of the silicon dioxide dispersions were added, followed by speed mixing at 3540 rpm for 20 minutes. In all experiments, homogeneous creams were obtained.

| Cream [g] | Silicon dioxide S80 dispersion (weight [g] and % by weight) | S80 proportion in Silicon dioxide/S80 dispersion [%] |
|---|---|---|
| 1.19 | 1.22 (50) | 10 |
| 1.40 | 0.27 (20) | 10 |
| 2.26 | 0.24 (10) | 40 |
| 2.24 | 0.23 (10) | 30 |
| 2.27 | 0.22 (10) | 15 |

Example 13: Facilitation of High-Pressure Homogenization by DAC Pretreatment 7.0 g of a mixture of hydrogenated egg phosphatidylcholine and cholesterol (55/45 mole %) existing as a solid solution was weighed into a PE cup (inner diameter about 51 mm) and admixed with 14 ml of a 5% mannitol solution. The mixture was subjected to speed mixing at 3540 rpm for 20 minutes, and then the now homogeneous mixture was subjected to high-pressure homogenization (3 cycles). The resulting VPG was redispersed, and the vesicle sizes were determined to be 28.9 nm (PCS), which corresponds to the usual particle size in a VPG prepared only by high-pressure homogenization (10 cycles).

Example 14: Preparation of Emulsions by Speed Mixing

Emulsions of soybean oil (10%) in water with phospholipid S75/S80 as emulsifier (2.4% and 1.2%) were prepared.

A) Emulsion with 2.4% Emulsifier.

2 ml of a dispersion of S75 (2.66 g of S75/l) was combined with 220 µl of soybean oil in a PE cup (inner diameter about 14 mm) and subjected to speed mixing at room temperature for 5, 10 and 15 minutes (3540 rpm). The emulsions were measured by PCS. After a mixing time of 10 minutes, the number of particles of >1 µm was also determined by means of the light obscuration method. For comparison, the lipid dispersion of the lipid emulsion Nutriflex® of the company B. Braun was also measured.

After 5 minutes already, an emulsion had formed having a particle size of about 50 nm, which did not changed even by further speed mixing. At a dilution of 1:20 million, the number of particles of >1 µm of the thus prepared emulsion was 48 (per ml). The Nutriflex® product had a similar number of particles in this size range (58, same dilution).

| Exp. | Mixing time | Particle size | Particles per ml (dilution 1:20 million) |
|---|---|---|---|
| 22a | 5 | 53.8 | 53 |
| 22b | 10 | 55.4 | 48 |
| 22c | 15 | 51.8 | 66 |
| NuTRIflex® | — | 197.0 | 58 |

B) Emulsion with 1.2% Emulsifier.

1 g of soybean oil and 120 mg of S80 were combined in a PE cup (inner diameter about 14 mm), and 1.8 g of glass beads (diameter 1 mm) and 1 ml of water was added. The mixture was heated at 60° C., followed by speed mixing for 5 minutes (3540 rpm). By adding 9 ml of water, the emulsion was adjusted to 10%. The particle size was determined to be 49.2 nm by means of PCS.

Example 15: Preparation of Solid Lipid Nanoparticles (SLN) by Speed Mixing

SLNs were prepared from trimyristine (10%) in water and tyloxapol as emulsifier (6%). In a PE cup (inner diameter about 34 mm), 1 g of trimyristine and 560 mg of tyloxapol was combined with 1,400 µl of water. 1.5 g of glass beads (diameter 1 mm) was added, and the mixture was heated at 80° C., followed by speed mixing at 3540 rpm for 5 minutes. The heating of the viscous mixture and the speed mixing were repeated three times. Subsequently, the dispersion was adjusted at 10% trimyristine by adding water and allowed to stand in the refrigerator at 4-6° C. for 12 hours. The particle size was determined to be 69.8 nm by means of PCS. At a dilution of 1:20 million, the number of particles of >1 µm of the thus prepared SLNs was only 9 particles. A lipid dispersion approved for clinical routine (Nutriflex® of B. Braun, see Example 1.12) had a substantially higher number of particles in this size range (58, same dilution).

Example 16: Redispersing by Means of DAC Mixing Device 125 mg of liposome gel prepared by speed mixing a mixture of 50 mg of hydrogenated egg phosphatidylcholine and cholesterol (55/45 mole %) and 75 µl of 5% mannitol solution as well as 100 mg of glass beads for 20 minutes was admixed with 250 µl of mannitol solution, added in an Eppi to the mixing vessel as in FIG. 3 into the speed mixer and subjected to speed mixing for 20 seconds. The redispersed liposome dispersion was homogeneous and free from large particles, and the mean size of the vesicles as determined by PCS was 74.2 nm.

Example 17: Tissue Maceration by Means of DAC

The method described in Example 16 can also be employed for breaking up biological samples (e.g., tissues). In particular, very small sample quantities can also be broken up with this technique. Thus, reception containers for sample vials suitable for low-temperature operation were prepared (see FIGS. 10 to 12) into which various types of so-called cryovials and Eppis can be clamped tightly. The following experiments were performed with 2 ml cryovial from Greiner. Thus, small pieces of tissue (flesh from cattle) were added to the cryovials, glass beads were added, the vials were closed and frozen in liquid nitrogen (for the type/amount of the glass beads and weight of the tissues, see Table 5).

Subsequently, the vials were pressed into the precooled reception container, which was inserted into the speed mixer and subjected to speed mixing at 3450 rpm for 30 seconds. Then, the vials were removed, their contents checked, and subsequently they were again subjected to speed mixing for 30 seconds. If necessary, cooling was again performed intermediately. This was repeated until the contents of the vials were a fine powder, or until the contents of the vials did no longer change visibly from interval to interval. The results are summarized in Table 5. The reddish-white tissue powder can be employed for further processing (e.g., lipid extraction or RNA extraction).

TABLE 5

Tissue maceration with speed mixer

| Experiment | Weight of tissue | Glass beads (diameter/amount) | Result |
|---|---|---|---|
| 1 | 82 mg | 1 mm, 103 mg | not easily broken down, large lumps, powdery surface |
| 2 | 55 mg | 3 mm, 136 mg/3 pieces | 60 seconds - fine powder |
| 3 | 55 mg | 5 mm, 171 mg/1 piece | 60 seconds - fine powder |
| 4 | 208 mg | 1 mm, 96 mg | not easily broken down, large lumps, powdery surface |
| 5 | 216 mg | 3 mm, 142 mg/3 pieces | 120 seconds - fine powder with small crumbs |
| 6 | 243 mg | 5 mm, 196 mg/1 piece | 90 seconds - fine powder |
| 7 | 69 mg | Mixture of 5 mm (1) and 1 mm (52 mg) | 60 seconds - fine powder |
| 8 | 232 mg | Mixture of 5 mm (1) and 1 mm (61 mg) | 60 seconds - fine powder |

The results show that small amounts, in particular, can be broken down quickly and completely in the vial employed here. However, the use of the appropriate breaking down aid is also important. In this experiment, the largest glass beads (here 5 mm) have proven to be the most favorable. Evidently, they have the greatest effect due to their weight, because the method is based on the acceleration of the breaking down aid. A combination of small and large glass beads has also proven favorable (see Table 5, Nos. 7 and 8). Here, good results could be achieved for both sample sizes (<100 mg/>200 mg).

In order to demonstrate the usefulness of this technique in the field of food analytics/control, a cheese (Parmigiano Reggiano of the company Gucina, 32% fat in dry matter (Aldi-Süd)) was converted to a fine yellowish-white powder by the above described technique. To achieve this, a total of 60 seconds of speed mixing at 3450 rpm was necessary. Two charges were performed (86 and 81 mg of Parmesan cheese), in which three 3 mm glass beads were added to one charge, and one 5 mm glass bead was added to the other. The results were undistinguishable.

In order to demonstrate the usefulness of this technique in the field of (pharmaceutical) analytics, half a tablet of Paracetamol-Ratiopharm® 500 was added to an Eppendorf vessel at room temperature for sample preparation. Two steel balls having a diameter of 3 mm served as a breaking down aid. By the technique described above, a fine white powder was produced within 30 seconds which could now be easily weighed in for further analytics. Thus, the technique can be used as a substitute for a mortar.

Example 18: Preparation of Liposomes in Injection Bottles

In future "bedside preparations" of liposomal formulations, injection bottles made of glass will be employed as judged from today's point of view. For this reason, experiments (i) relating to the influence of the lipid concentration during speed mixing, (ii) relating to the influence of the speed mixing time and (iii) relating to the influence of different homogenization aids (glass beads with different diameters) on the homogenization result (vesicle size) were performed on the basis of such vessels (25 ml injection bottle, outer diameter 36 mm).

Figure 6A:
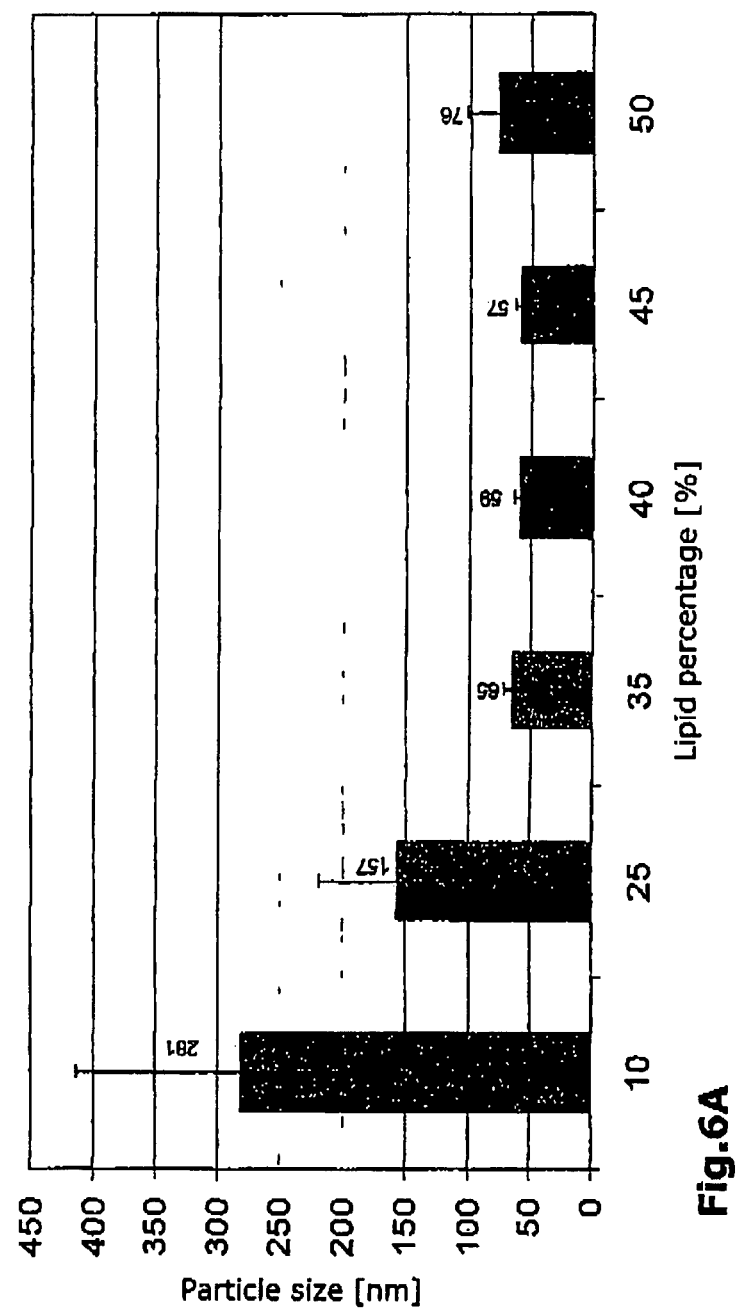
FIG. 6: influence of various parameters on the particle size in speed mixing within an injection bottle (cf. example 18): A) variation of lipid concentration; B) varying speed-mix times and C) glass beads having different sizes as dispersing aid FIG. 7 influence of the speed mixer speed on the particle size

(i) Influence of Lipid Concentration:

Each charge contained 0.5 g of a mixture of hydrogenated egg phosphatidylcholine and cholesterol (55/45 mole %) existing as a solid solution as well as 0.5 g of glass beads (diameter 1 mm) as a homogenization aid. 0.9% saline was added in such an amount that dispersions with 10, 25, 35, 40, 45 and 50% by weight of lipid were produced. These dispersions were respectively subjected to speed mixing at 3540 rpm for 20 min, and then the vesicle sizes were determined by means of PCS. Each experiment was performed four times. The results are shown in FIG. 6A. It was found that the smallest vesicles (57-65 nm) can be prepared with lipid concentrations of 35-45%. In this range of concentrations, the results are also best reproducible, which can be seen from the small standard deviations.

(ii) Influence of Speed Mixing Time:

The procedure was as described under (i), but in all experiments, an identical lipid concentration of 40% was used. The speed mixing times were 1, 5, 10, 15, 20, 30, 40 and 50 min. A reduction of the vesicle sizes with increasing speed mixing time could be shown (FIG. 6B). After 1 min, very large vesicles with a heterogeneous size distribution were predominant. After 5 minutes already, vesicles having a size of smaller than 80 nm could be detected. After 50 minutes, the vesicles had a size which was just above 50 nm and was not much different from the sizes at 30 and 40 minutes of speed mixing time.

Figure 6C:
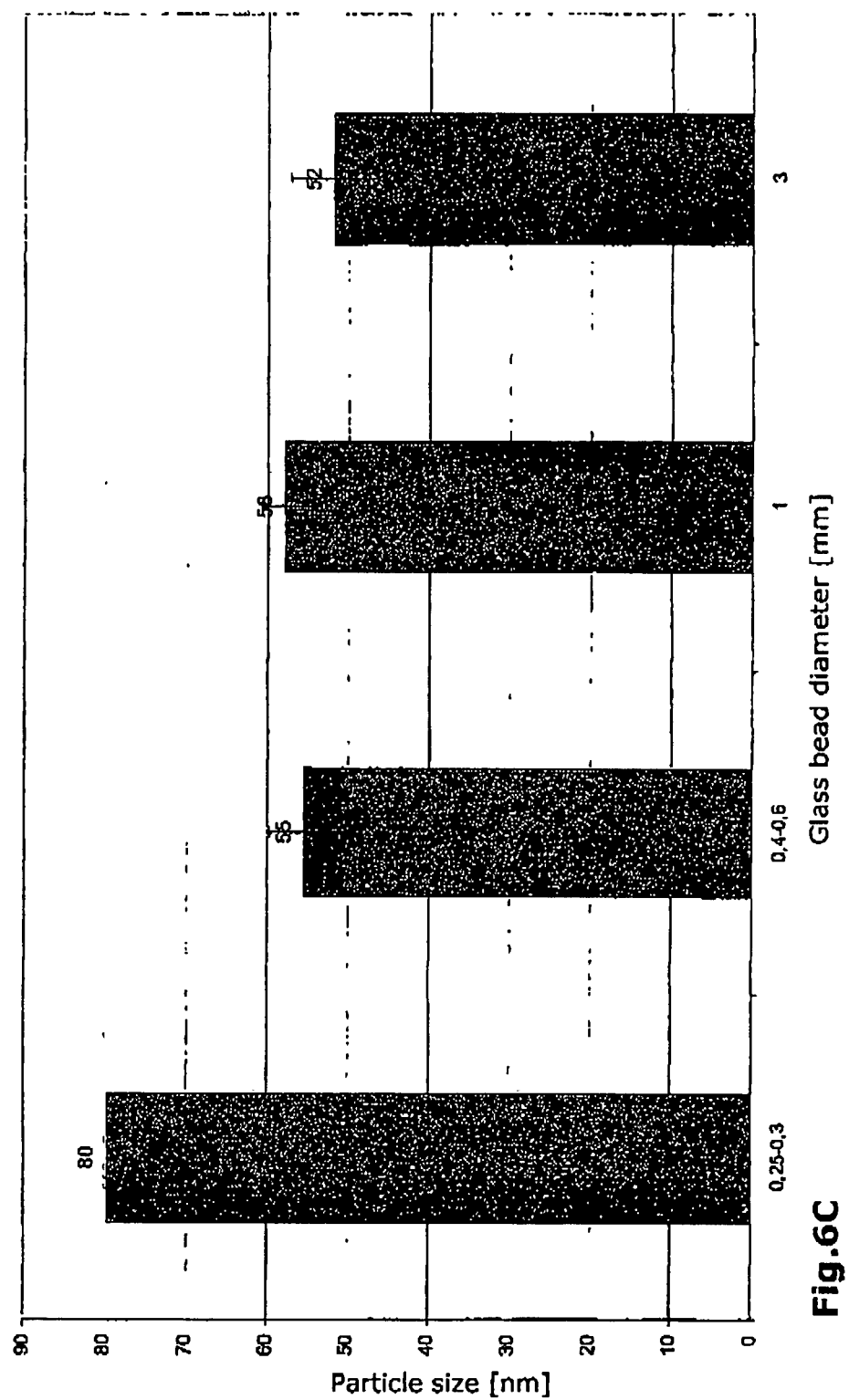

(iii) Influence of the Dispersing Aids:

The procedure was as described under (ii), but in all experiments, an identical lipid concentration (40%) and the same speed mixing time (30 min) was used. The kind of glass beads that were added to the lipid mixtures as shaking aids was varied. 0.5 g each of glass beads having diameters of 0.25-3 mm, 0.4-0.6 mm, 1 mm or 3 mm was added. It could be shown that the glass beads having the smallest diameter led to the poorest homogenization result, the vesicles having a size of about 80 nm (FIG. 6C). Glass beads of 0.4 mm to 3 mm did not show any significantly different effect on the homogenization result, the vesicle sizes being from 52 to 58 nm.

Example 19: Dependence of the Achievable Vesicle Sizes on the DAC Speed

In order to show the dependence of the particle sizes on the speed of the speed mixer and thus on the intensity of the homogenization process, liposomes were prepared as described in Example 18 (liposome preparation in injection bottles). Speed mixing was always performed for 20 min, and the speed mixing speed was varied in the experiments from 2000 rpm to 3450 rpm, i.e., the maximum speed of the available speed mixer. The counter-rotation ratio was constantly at 4.2:1. The results of these experiments are shown in FIG. 7.

The examination shows that the vesicle sizes that can be achieved depend on the speed mixing speed, and that smaller vesicle sizes can be achieved by increasing the speed mixing speed. Relevant speeds for the preparation of small vesicles of below 100 nm, in particular, are within a range of above 2000 rpm. By calculating a fitted function, it can be additionally shown that particle sizes within a range of 30 nm should be realizable when the speed is increased further (from 4000 to 5000 rpm).

Example 20: Working with Small Scales

An important aspect of the preparation of lipid-based nanoparticles, such as liposomes, is the fact that the DAC technique may be used to also process quite small amounts, as required in animal experiments or in the field of cell cultures, under sterile conditions. In order to show this, an experiment was performed in which liposomes were prepared from an EPC-3/cholesterol mixture (see Example 1) in a 10 ml sample glass with a crimp top (type N20-10 DIN (10 ml), Macherey-Nagel) that can be filled and flange-sealed under sterile conditions. As the scales, 40, 20, 10 and 5 mg of lipid were chosen. In addition, 120 mg of glass beads (diameter 1 mm) was added to each vial as a homogenization aid. To each vial, 0.9% saline was added, the volume corresponding to 150% of the weight of the weighed-in lipid. The lipid weights and the added amount of liquid are shown in Table 6. The samples were subjected to speed mixing for 30 s each and then allowed to stand at room temperature for 25 min. Subsequently, the samples were again subjected to speed mixing at 3450 rpm for 5 min. Saline was used for diluting to a lipid content of 10 mM (addition of 6.86 ml, 3.43 ml, 1.80 ml or 0.95 ml of saline, followed by speed mixing for 3 min), and then the vesicle sizes were determined by means of PCS (Table 6). All vesicle sizes, also those of the very small scales, were mutually comparable and very small in addition.

TABLE 6

Vesicle sizes for small scales

| Experiment | Amount of lipid | Volume of 0.9% saline | Vesicle size |
| --- | --- | --- | --- |
| 1 | 39.9 mg | 59.9 µl | 51.2 nm |
| 2 | 10.02 mg | 30.0 µl | 49.8 nm |
| 3 | 10.48 mg | 15.7 µl | 44.2 nm |
| 4 | 5.53 mg | 8.3 µl | 51.5 nm |

The invention claimed is:

1. A process for forming lipid-based nanoparticles or liposomes which comprises homogenizing a lipid component with an aqueous component in a dual asymmetric centrifuge (DAC) for a centrifugation time, wherein the lipid component comprises one or more compounds selected from the group consisting of amphiphiles, lipids, detergents, and emulsifiers.

2. The process of claim 1, wherein the process is performed with a g-number of at least 1.2 g.

3. The process of claim 1, wherein the process is performed with a counter-rotation ratio of from 1:6 to 6:1.

4. The process of claim 1, wherein the centrifugation time is from 30 s to 1 h.

5. The process of claim 1, wherein a mixing aid is used.

6. The process of claim 5, wherein the mixing aid is glass beads having a diameter of from 0.5 to 6 mm.

7. The process of claim 1, wherein the lipid component comprises at least one lipid selected from the group consisting of phospholipids, glycolipids, cholesterols, sphingolipids, polyethylene glycol lipid derivatives, cationic lipids, triglycerides and waxes.

8. The process of claim 1, wherein the aqueous component is selected from the group consisting of water, an aqueous alcoholic solution, an aqueous buffer containing solution and an aqueous alcoholic buffer containing solution.

9. The process of claim 1, wherein the lipid and/or the aqueous component contains one or several functional lipophilic or hydrophilic substances selected from the group consisting of pharmaceutically active, diagnostically relevant, cosmetically active, biosynthetic compounds and compounds relevant for chemical synthesis.

10. The process of claim 1, wherein the lipid-based nanoparticles are manufactured by charging a vessel with one of both components and subsequently adding the other component during the homogenization in the DAC.

11. The process of claim 1, wherein a mixture of the lipid component and the aqueous component is homogenized in the DAC.

12. The process of claim 1, wherein the process comprises introducing an aqueous component into a preformed dispersion of lipid-based nanoparticles (redispersion).

13. The process of claim 1, wherein injection bottles are used as vessels.

14. The process of claim 1, wherein vessels having a diameter of from 5 to 75 mm are used.

15. The process of claim 1, wherein the lipid-based nanoparticles are liposomes including vesicular phospholipid gels (VPG).

16. The process of claim 15, wherein the concentration of the lipid component is from 1 to 600 mM.

17. The process of claim 15, wherein the lipid component is selected from the group consisting of phospholipids, cholesterol and cationic lipids.

18. The process of claim 15, wherein the lipid component is a phosphatidylcholine.

19. The process of claim 1, wherein the lipid-based nanoparticles are droplets in emulsions.

20. The process of claim 19, wherein the lipid-based nanoparticles are droplets in nanoemulsions.

21. The process of claim 20, wherein the nanoemulsions contain from 10 to 20% (weight/vol.) of oil and from 0.5 to 2.5% (weight/vol) of lecithin or polymer emulsifiers.

22. The process of claim 20, wherein the nanoemulsions contain one or more water-insoluble active substances.

23. The process of claim 22, wherein said one or more water-insoluble active substances are selected from the group consisting of taxanes, amphotericine B, campthotecine and dekapeptides.

24. The process of claim 1, wherein the lipid-based nanoparticles are solid lipid nanoparticles (SLN).

25. The process of claim 24, wherein the SLN are manufactured at temperatures exceeding room temperature.

26. The process of claim 24, wherein the SLN contain triglycerides and/or waxes as lipid component.

27. The process of claim 24, wherein the SLN contain water-insoluble active substances.

28. The process of claim 27, wherein said water-insoluble active substances are selected from the group consisting of taxanes, amphotericine B, camptotecine and dekapeptides.

29. The process of claim 1, further comprising incorporating an active substance into a preformed liposome for passive loading or further comprising incorporating a nucleic acid into a preformed liposome to form a lipoplex.

30. The process of claim 29, wherein the active substance used for passive loading is selected from the group consisting of gemcitabine, vincristine, vindesin and platinum compounds.

31. The process of claim 29, wherein the nucleic acid used to form a lipoplex is selected from the group consisting of cDNA, siRNA and dsRNA.

32. The process of claim 1, further comprising screening lipid-based nanoparticles in the field of preformulation.

33. The process of claim 1, further comprising incorporating compounds in preformed lipid-based nanoparticles in the Dual Asymmetric Centrifuge (DAC).

34. A process for forming a lipid-based nanoparticle, the process comprising homogenizing a lipid component with an aqueous component in a dual asymmetric centrifuge (DAC) for a centrifugation time, wherein the lipid component is not preformed as a lipid-based nanoparticle prior to homogenization.

* * * * *